(12) United States Patent
Kehne et al.

(10) Patent No.: US 6,331,506 B1
(45) Date of Patent: *Dec. 18, 2001

(54) DISUBSTITUTED METHYLIDENE HYDRAZINOPHENYL SULFONYLUREAS, PROCESS FOR THEIR PRODUCTION AND THEIR USE AS HERBICIDES AND PLANT GROWTH REGULATORS

(75) Inventors: Heinz Kehne; Lothar Willms, both of Hofheim; Klaus Bauer, Hanau; Hermann Bieringer, Eppstein; Christopher Rosinger, Hofheim, all of (DE)

(73) Assignee: Hoechst Schering AgrEvo GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,961

(22) PCT Filed: Mar. 12, 1997

(86) PCT No.: PCT/EP97/01244

§ 371 Date: Sep. 16, 1998

§ 102(e) Date: Sep. 16, 1998

(87) PCT Pub. No.: WO97/35863

PCT Pub. Date: Oct. 2, 1997

(30) Foreign Application Priority Data

Mar. 12, 1997 (DE) ................................. 196 11 355

(51) Int. Cl.⁷ .................... C07D 239/48; C07D 239/47; C07D 239/52; A01N 43/54
(52) U.S. Cl. .................... 504/214; 504/215; 540/601; 544/295; 544/296; 544/122; 544/123; 544/321; 544/323; 544/324; 544/331; 544/332
(58) Field of Search ................ 504/214, 215; 544/331, 332, 96, 295, 296, 122, 323; 540/601

(56) References Cited

U.S. PATENT DOCUMENTS

| | | | |
|---|---|---|---|
| 5,059,238 | * 10/1991 | Arabori et al. | 71/93 |
| 5,449,812 | 9/1995 | Schnabel et al. | 560/13 |
| 5,723,409 | * 3/1998 | Schnabel et al. | 504/214 |
| 5,849,666 | * 12/1998 | Kehne et al. | 504/204 |
| 5,922,645 | * 7/1999 | Kehne et al. | 504/214 |
| 5,922,646 | * 7/1999 | Schnabel et al. | 504/214 |

FOREIGN PATENT DOCUMENTS

| | | |
|---|---|---|
| 4442229 A1 | 5/1996 | (DE) . |
| 0382437 A1 | 8/1990 | (EP) . |
| 0562575 A2 | 9/1993 | (EP) . |
| 95/10045 | 7/1996 | (ZA) . |

* cited by examiner

Primary Examiner—John M. Ford
(74) Attorney, Agent, or Firm—Frommer Lawrence & Haug LLP

(57) ABSTRACT

Disubstituted methylidenehydrazinophenylsulfonylureas, processes for their preparation and their use as herbicides and plant growth regulators Compounds of the formula (I) and salts thereof

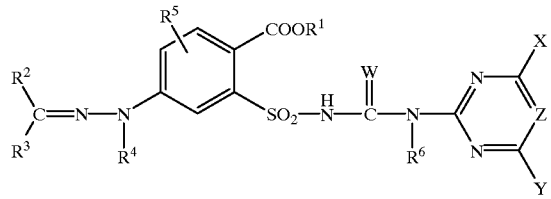

(I)

in which $R^1$ to $R^6$, W, X, Y, Z are as defined in claim 1 and the group $R^2R^3C$ is a carbon atom which is subsituted by at least one electron-withdrawing radical $R^2$ or $R^3$ are suitable as herbicides and plant growth regulators. They can be prepared in accordance with known processes via intermediates, some of which are novel.

6 Claims, No Drawings

DISUBSTITUTED METHYLIDENE HYDRAZINOPHENYL SULFONYLUREAS, PROCESS FOR THEIR PRODUCTION AND THEIR USE AS HERBICIDES AND PLANT GROWTH REGULATORS

This is a 371 of PCT/EP97/01244, filed Mar. 12, 1997.

It is known that phenylsulfonylureas having hydrazine partial structures have herbicidal properties. These are primarily hydrazones (EP-A-382 437, EP-A-562 575) or heterocycles having an incorporated hydrazine structure (EP-A-382 436, EP-A-384 602).

In the German Patent Applications No. P 44 42 229.6 an No. 19 521 668.7, phenylsulfonylureas have already been preposed which have carboxy(derivative) groups or sulfur substituents in position 2 and which are substituted with hydrazone radicals in position 5.

Surprisingly, there have now been found phenylsulfonylureas having certain hydrazone radicals carrying electron-withdrawing substituents which are particularly suitable as herbicides or plant grog regulators.

The present invention accordingly provides compounds of the formula (I) or salts thereof

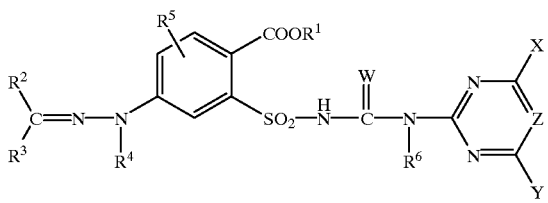

(I)

in which
R$^1$ is H or a hydrocarbon radical which is unsubstituted or substituted, or a heterocyclyl radical which is unsubstituted or substituted, where each of the two last-mentioned radicals including substituents has preferably 1 to 20 carbon atoms,
  a) R$^2$ is CN, NO$_2$ or acyl preferably having 1 to 20 carbon atoms and
  R$^3$ is CN, NO$_2$, acyl preferably having 1 to 20 carbon atoms, CF$_3$, aryl or a heterocyclic radical, where each of the two last-mentioned radicals is unsubstituted or substituted, or
  b) R$^2$R$^3$C together form a carbocyclic or heterocyclic ring Which has at least one carbon atom substituted by an oxo group in a position adjacent to the carbon atom in position 1 of the group CR$^2$R$^3$, or
  c) R$^2$ is NO$_2$ or [(C$_1$–C$_4$)alkyl]carbonyl and R$^3$ is H or (C$_1$–C$_4$)alkyl,
R$^4$ is H, an unsubstituted or substituted aliphatic hydrocarbon radical having 1 to 6 carbon atoms in the hydrocarbon moiety and one or more substituents, where the substituents are selected from the group consisting of halogen, (C$_1$–C$_4$)alkoxy, (C$_1$–C$_4$)alkylthio, (C$_1$–C$_4$)alkylsulfonyl, [(C$_1$–C$_4$)alkyl]carbonyl, [(C$_{14}$)alkoxy]carbonyl, CN, substituted and unsubstituted phenyl and (C$_3$–C$_6$)cycloalkyl, or is (C$_3$–C$_6$)alkenyl or (C$_3$–C$_6$)alkynyl or an acyl radical preferably having 1 to 20 carbon atoms,
R$^5$ is H, halogen, NO$_2$, CN, (C$_1$–C$_4$alkyl, (C$_1$–C$_4$)alkoxy, [(C$_1$C$_4$)alkyl]carbonyl or [(C$_1$–C$_4$)alkoxy]carbonyl, where each of the four last-mentioned radicals is unsubstituted or substituted in the alkyl moiety by one or more halogen atoms,
R$^6$ is H or (C$_1$–C$_4$)alkyl, preferably H or CH$_3$,
W is an oxygen or sulfur atom, preferably an oxygen atom,
X, Y independently of one another are H, halogen, (C$_1$–C$_4$)alkyl, (C$_1$–C$_4$)alkoxy, (C$_1$–C$_4$)alkylthio, where each of the 3 last-mentioned radicals is unsubstituted or substituted by one or more radicals selected from the group consisting of halogen, (C$_1$–C$_4$)alkoxy and (C$_1$–C$_4$)alkylthio, or is mono- or di[(C$_1$–C$_4$)alkyl] amino, (C$_3$–C$_6$)cycloalkyl, (C$_2$–C$_5$)alkenyl, (C$_3$–C$_5$) alkynyl, (C$_3$–C$_5$)alkenyloxy or (C$_2$–C$_5$)alkynyloxy and
Z is CH or N.

The compounds of the formula (I) can form salts where the hydrogen of the —SO$_2$—NH— group is replaced by an agriculturally suitable cation. These salts are, for example, metal salts, in particular alkali metal salts or alkaline earth metal salts, in particular sodium and potassium s or else ammonium salts and salts with organic amines. Likewise salt formation. may occur by addition of an acid to basic groups, such as, for example, amino and alkylamino. Acids which are suitable for this purposes are strong inorganic and organic acids, for example HCl, HBr, H$_2$SO$_4$ or HNO$_3$.

In the formula (I) and all subsequent formulae, the radicals alkyl, alkoxy, haloalkyl, haloalkoxy, alkylamino and alkylthio and the corresponding unsaturated and/or substituted radicals can in each case be straight-chain or branched in the carbon skeleton. Unless specifically indicated, the lower carbon skeletons, for example those having 1 to 6 carbon atoms or, in the case of unsaturated groups, 2 to 6 carbon atoms, a for these radicals. Alkyl radicals, also in the composite meaning such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the unsaturated radicals which are possible and which correspond to the alkyl radicals, alkenyl is, for example, allyl, 1-methylprop-2-en-1-yl, 2-methylprop-2-en-1-yl but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methyl-but-3-yn-1-yl.

Alkenyl in the form "(C$_3$–C$_4$)alkenyl" or "(C$_3$–C$_6$) alkenyl" is preferably an alkenyl radical having 3 to 4 or 3 to 6 carbon atoms in which the double bond is not positioned at the carbon atom attached to the remainder of the molecule of the compound (I) ("yl" position). The same applies correspondingly to (C$_3$–C$_4$)alkynyl etc.

Cycloalkyl is a carbocyclic, saturated ring system having 3–8 carbon atoms, for example cyclopropyl, cyclopentyl or cyclohexyl.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; the same applies correspondingly to haloalkenyl and other halogen-substituted radicals.

A hydrocarbon radical is a straight-chain, branched or cyclic, saturated or unsaturated, aliphatic or aromatic hydrocarbon radical, for example alkyl, alkenyl, alkynyl, cycloalkyl, cycloalkenyl or aryl; aryl is a mono-, bi- or polycyclic aromatic system, for example phenyl, naphthyl, tetrahydronaphthyl, indenyl, indanyl, pentalenyl, fluorenyl and the like, preferably phenyl;

a hydrocarbon radical is preferably alkyl, alkenyl or alkynyl having up to 12 carbon atoms or cycloalkyl having 3, 4, 5, 6 or 7 ring atoms or phenyl; this applies correspondingly to a hydrocarbon radical in a hydrocarbonoxy radical.

A heterocyclic radical or ring (heterocycyl) may be saturated, unsaturated or heteroaromatic; it preferably contains one or more hetero units in the ring, preferably selected from the group consisting of N, O, S, SO, $SO_2$; it is preferably an aliphatic heterocyclic radical having 3 to 7 ring atoms or a heteroaromatic radical having 5 or 6 ring atoms and contains 1, 2 or 3 hetero units. For example, the heterocyclic radical may be a heteroaromatic radical or ring (heteroaryl), such as, for example, a mono-, bi- or polycyclic aromatic system in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical, such as oxiranyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group may also be located on the hetero ring atoms which can exist at various oxidation levels, for example in the case of N and S.

Substituted radicals, such as substituted hydrocarbon radicals, for example substituted alkyl, alkenyl, alkynyl, aryl, phenyl and benzyl, or substituted heterocycyl or heteroaryl are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl and unsaturated aliphatic radicals, such as alkenyl, alkynyl, alkenyloxy, alkynyloxy and the like, which correspond to the abovementioned saturated hydrocarbon-containing radicals. Among radicals having carbon atoms, those having 1 to 4 carbon atoms, in particular 1 or 2 carbon atoms, are preferred. Preferred substituents are, in general, selected from the group consisting of halogen, for example fluorine and chlorine, $(C_1–C_4)$alkyl, for example methyl or ethyl, $(C_1–C_4)$haloalkyl, preferably trifluoromethyl, $(C_1–C_4)$alkoxy, preferably methoxy or ethoxy, $(C_1–C_4)$haloalkoxy, nitro and cyano. Especially preferred in this context are the substituents methyl, methoxy and chlorine.

Mono- or disubstituted amino is a chemically stable radical from the group of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and also N-heterocycles; preference in this context is given to alkyl radicals having 1 to 4 carbon atoms; aryl is preferably phenyl or substituted phenyl; for acyl, the definition given further below applies; preferably $(C_1–C_4)$alkanoyl. This applies correspondingly to substituted hydroxylamino or hydrazino.

Optionally substituted phenyl is preferably phenyl which is unsubstituted or mono- or polysubstituted, preferably up to trisubstituted, by identical or different radicals selected from the group consisting of halogen, $(C_1–C_4)$alkyl, $(C_1–C_4)$alkoxy, $(C_1–C_4)$haloalkyl, $(C_1–C_4)$haloalkoxy and nitro, for example o-, m- and p-tolyl, dimethylphenyls, 2-, 3- and 4-chlorophenyl, 2-, 3- and 4-trifluoro and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid and radicals of acids derived therefrom, such as thiocarboxylic add, optionally N-substituted iminocarboxylic acids or the radical of carbonic monoesters, optionally N-substituted carbamic acid, sulfonic acids, sulfinic acids, phosphonic adds, phosphinic acids. Acyl is, for example, formyl, alkylcarbonyl such as $(C_1–C_4$alkyl$)$carbonyl, phenylcarbonyl, where the phenyl ring may be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also relates to all stereoisomers which are embraced by the formula (I) and to their mixtures. Such compounds of the formula (I) contain one or more asymmetric carbon atoms or else double bonds which are not separately indicated in formula (I). The stereoisomers which are possible and which are defined by their specific spatial form, such as enantiomers, diastereomers and Z and E isomers, are all embraced by formula (I) and can be obtained from mixtures of the stereoisomers by customary methods, or else prepared by stereoselective reactions in combination with the use of stereochemically pure starting materials.

The abovementioned examples of radicals or ranges of radicals which come under the general terms such as "alkyl", "acyl", "substituted radicals" etc., are not a complete enumeration. The general terms also embrace the definitions of ranges of radicals in groups of preferred compounds mentioned further below, in particular ranges of radicals which include specific radicals from the examples given in the tables.

Compounds of the formula (I) or salts thereof according to the invention which are of particular interest primarily for reasons of more potent herbicidal activity, better selectivity and/or because they can be prepared more easily, are those in which $R^1$ is H, $(C_1–C_6)$alkyl, $(C_3–C_6)$alkenyl, $(C_3–C_6)$alkynyl where each of the three last-mentioned radicals is unsubstituted or substituted by one or more radicals selected from the group consisting of halogen, phenyl, $(C_1–C_4)$alkoxy, $(C_1–C_4)$alkylthio and $[(C_1–C_4)$alkoxy$]$carbonyl, or is $(C_3–C_6)$cycloalkyl, $(C_3–C_6C)$cycloalkyl $(C_1–C_3)$alkyl, heterocyclyl having 3 to 6 ring atoms or heterocycyl$(C_1–C_3)$alkyl having 3 to 6 ring atoms, where each of the 4 last-mentioned radicals is unsubstituted or substituted by one or more radicals selected from the group consisting of halogen, $(C_1–C_4)$alkyl and $(C_1–C_4)$alkoxy, a) $R^2$ is $[(C_1–C_4)$alkyl$]$carbonyl which is unsubstituted or substituted by one or more radicals selected from the group consisting of halogen, $(C_1–C_4)$alkoxy, $(C_1–C_4)$althio and phenyl, or is $[(C_1–C_4)$alkoxy$]$ carbonyl which is unsubstituted or substituted by one or more radicals selected from the group consisting of halogen, $(C_1–C_4)$alkoxy, phenoxy and phenyl, or is $CONR^7R^8$, CHO, CN, $NO_2$ or phenylcarbonyl which is unsubstituted or substituted by one or more radicals selected from the group consisting of halogen, $(C_1–C_4)$alkyl, $(C_1–C_4)$haloalkyl, $(C_1–C_4)$ alkoxy, $(C_1–C_4)$alkylthio, CN and $NO_2$, or is $(C_1–C_4)$alkylsulfonyl, $(C_1–C_4)$haloalkylsulfonyl or —P(O)[O$(C_1–C_4)$alkyl]$_2$ and $R^3$ is as defined under $R^2$ or is $CF_3$ or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$alkylthio, $(C_1-C_4)$alkylsulfonyl, $[(C_1-C_4)$alkoxy]carbonyl, CN and $NO_2$, or b) $R^2R^3C$ together form a ring having 5 to 8 ring atoms, which is carbocyclic or heterocyclic and has one or two heteroatoms selected from the group consisting of N, O and S and which is substituted by one or two oxo groups, in each case in the position alpha to the carbon atom in position 1 of the group $CR^2R^3$ and additionally unsubstituted or additionally substituted by one or more radicals selected from the group consisting of $(C_1-C_4)$alkyl, $(C_1-C_4)$haloalkyl, halogen and oxo, or c) $R^2$ is $NO_2$ or $[(C_1-C_4)$alkyl]carbonyl and $R^3$ is H or $(C_1-C_4)$alkyl, $R^4$ is H or $(C_1-C_6)$alkyl which is unsubstituted or substituted by one or more radicals selected from the group consisting of halogen, $(C_1-C_4)$alkoxy, $(C_1-C_4)$alkylthio, $(C_1-C_4)$alkylsulfonyl $[(C_1-C_4)$ alkoxy]carbonyl, CN, phenyl and $(C_3-C_6)$ cycloalkyl, or is $(C_3-C_6)$alkenyl or $(C_3-C_6)$ alkynyl, where each of the two last-mentioned radicals is unsubstituted or substituted by one or more halogen atoms, or is a group of the formula

R* is H, $(C_1-C_8)$alkyl, $(C_2-C_6)$alkylenyl, where each of the three last-mentioned radicals is unsubstituted or substituted by one or more radicals selected from the group consisting of halogen, $(C_1-C_4)$alkoxy, $(C_1-C_4)$alkylthio, phenoxy, $[(C_1-C_4)$alkoxy]carbonyl, unsubstituted and substituted heterocyclyl and unsubstituted and substituted phenyl, or is unsubstituted or substituted $(C_3-C_6)$cycloalkyl, unsubstituted or substituted phenyl, unsubstituted or substituted heterocycyl or $[(C_1-C_4)$ alkoxy]carbonyl, R** is $(C_1-C_6)$alkyl, $(C_3-C_6)$alkenyl, $(C_3-C_6)$ alkynyl, where each of the three last-mentioned radicals is unsubstituted or substituted by one or more radicals selected from the group consisting of halogen, $(C_1-C_4)$alkoxy, $(C_1-C_4)$alkylthio and phenyl, or is phenyl which is unsubstituted or substituted by one or more radicals selected from the group consisting of halogen, CN, $NO_2$, $(C_1-C_4)$alkyl, $(C_1-C_4)$haloalkyl and $(C_1-C_4)$alkoxy, $R^7$ and $R^8$ independently of one another are H, $(C_1-C_4)$alkyl, $(C_3-C_4)$alkenyl, $(C_3-C_4)$ alkynyl or phenyl which s unsubstituted or substituted by one or more radicals selected from the group consisting of halogen, $(C_1-C_4)$ alkyl, $(C_1-C_4)$haloalkyl, $(C_1-C_4)$alkoxy $(C_1-C_4)$alkylthio, $(C_1-C_4)$alkylsulfonyl, $[(C_1-C_4)$alkoxy]arbonyl, CN and $NO_2$, or $R^7$ and $R^8$ together with the nitrogen atom form a heterocyclic ring having 5 or 6 ring members, which may, if appropriate,contain further heteroatoms selected from the group consisting of N, O and S and which is unsubstituted or mono- or polysubstituted by $(C_1-C_4)$alkyl or an oxo group, W is O or S, preferably O, X and Y Independently of one another are H, halogen, $(C_1-C_4)$alkyl $(C_1-C_4)$alkoxy, $(C_1-C_4)$alkylthio, where each of the three last-mentioned radicals is unsubstituted or substituted by one or more radicals selected from the group consisting of halogen, $(C_1-C_3)$alkoxy and $(C_1-C_4)$alkylthio, mono or di$[(C_1-C_4)$ alkyl]amino, $(C_3-C_6)$cycloalkyl, $(C_3-C_5)$ alkenyl, $(C_3-C_5)$alkenyloxy or $(C_3-C_5)$ alkynyloxy and Z is CH or N.

Of particular interest are also compounds of the formula (I) and salts thereof according to the invention in which $R^1$ is $(C_1-C_6)$alkyl which is unsubstituted or substituted by one or more radicals selected from the group consisting of halogen and $(C_1C_4)$alkoxy, or is 3-oxetanyl, $(C_3-C_4)$alkenyl or $(C_3-C_4)$alkynyl, a) $R^2$ and $R^3$ independently of one another are $[(C_1-C_4)$ alkyl]carbonyl, $[(C_1-C_4)$alkoxyl]carbonyl, $CONR^7R^8$, CHO, CN, $NO_2$, benzoyl or $(C_1-C_4)$ alkylsulfonyl or b) $CR^2R^3$ together form a ring having 5 to 8 ring atoms, which is carbocyclic or heterocyclic and has one or two heteroatoms selected from the group consisting of N, O and S and which is substituted by one or two oxo groups, in each case in the position alpha to the carbon atom in position 1 of the group $CR^2R^3$ and additionally unsubstituted or additionally substituted by one or more radicals selected from the group consisting of $(C_1-C_4)$alkyl, $(C_1-C_4)$haloalkyl and halogen, or c) $R^2$ is $NO_2$ or $[(C_1-C_4)$alkyl]carbonyl and $R^3$ is H or $(C_1-C_4)$alkyl, $R^4$ is H, $(C_1-C_4)$alkyl which is unsubstituted or substituted by one or more radicals selected from the group consisting of halogen, $(C_1-C_4)$alkoxy. $(C_1-C_4)$alkylthio, $[(C_1-C_4)$alkoxy]carbonyl and phenyl or is $(C_3-C_4)$alkenyl or $(C_3-C_4)$alkynyl, $R_5$ is H, $(C_1-C_4)$alkyl, $(C_1-C_4)$haloalkyl, $(C_1-C_4)$ alkoxy or halogen, X and Y independently of one another are $(C_1-C_4)$ alkyl, $(C_1-C_4)$alkoxy, where each of the two last-mentioned radicals is unsubstituted or subsituted by one or more halogen atoms, or are $(C_1-C_4)$ alkylthio, halogen or mono- or di$[(C_1-C_2)$alkyl] amino and W is an oxygen atom.

Preferred compounds of the formula (I) or salts thereof are those in which $R^4$ is H, $R^5$ is H, $(C_1-C_4)$alkyl or halogen, X is $(C_1-C_2)$alkyl, $(C_1-C_2)$alkoxy, $(C_1-C_2)$alkylthio, $(C_1-C_2)$haloalkyl or $(C_1-C_2)$haloalkoxy and Y is $(C_1-C_2)$alkyl, $(C_1-C_2)$alkoxy, halogen, $NHCH_3$ or $N(CH_3)_2$.

Particularly preferred compounds of the formula (I) or salts thereof are those in which $R^1$ is methyl or ethyl, $R^2$ and $R^3$ independently of one another are $[(C_1-C_2)$ alkoxy]carbonyl, CN or $NO_2$, or CR²R³ together form a ring having 5 or 6 ring atoms, which is carbocyclic or heterocyclic and has one or two heteroatoms selected from the group consisting of N, O and S and which is substituted by one or two oxo groups, in each case in the position alpha to the carbon atom in position 1 of the group CR²R³, and which is additionally unsubstituted or additionally substituted by one or more (C₁–C₂)alkyl radicals, and R⁵ is H.

The present invention also provides processes for prepading the compounds of the formula (I) or salts thereof according to the invention which comprise a) reacting a compound of the formula (II)

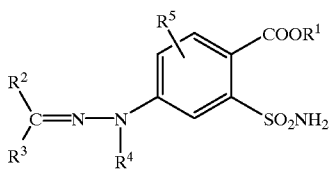

(II)

with a heterocyclic carbamate of the formula (III),

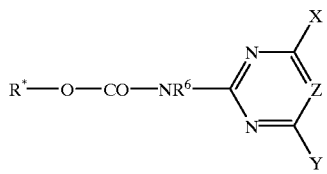

(III)

in which R* is phenyl with or without substitution or (C₁–C₄)alkyl, or b) reacting a sulfonylcarbamate of the formula (IV),

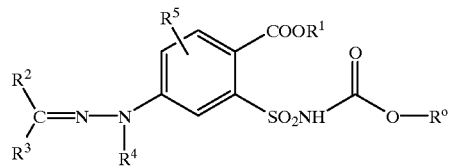

(IV)

in which R⁰ is phenyl with or without substitution or (C₁–C₄)alkyl, with an aminoheterocycle of the formula (V)

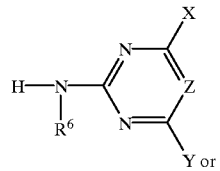

(V)

c) reacting a sulfonyl isocyanate of the formula (VI)

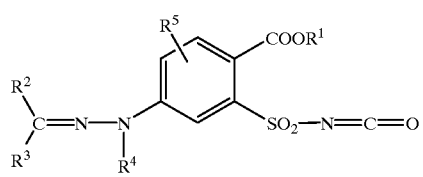

(VI)

with an aminoheterocycle of the formula (V) or d) reacting a sulfonamide of the formula (II) with a (thio)isocyanate of the formula (VII)

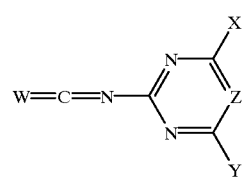

(VII)

in the presence of a base or e) reacting an aminoheterocycle of the formula (V) initially with a carbonic ester, for example diphenyl carbonate, under base catalysis and reacting the formed intermediate in a one pot reaction with a sulfonamide of the formula (II) (see variant a), where in the formulae (II)–(VII), the radicals or groups R¹—R⁶, W, X, Y and Z are as defined in formula (I) and in process variants a) to c) and e) compounds (I) where W=O are initially obtained.

The reaction of the compounds of the formulae (II) and (III) is preferably carried out base-catalyzed in an inert organic solvent, such as, for example, dichloromethane, acetonitrile, dioxane or THF at temperatures between 0° C., preferably 20° C., and the boiling point of the solvent. Suitable bases are, in this context, for example, organic amine bases, such as 1,8diazabicyclo[5.4.0]undec-7-ene (DBU) or alkali metal hydroxides, such as, for example, NaOH, in particular if R⁰=(subst.) phenyl (cf. EP-A-44807), or trimethylaluminum or trimethylaluminum, the latter in particular if R⁰=alkyl (cf. EP-A-166 516). The base in question is employed, for example, in the range of from 1 to 3 molar equivalent, based on the compound of the formula (II).

The sulfonamides (II) are novel compounds. They and their preparation also form part of the subject matter of the present invention.

The compounds of the formula (II) are obtained, for example, starting from compounds of the formula (VIII),

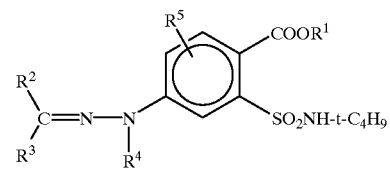

(VIII)

in which $R^1$—$R^5$ are as defined in formula (I) by reaction with a strong acid (cf. in this context WO 89/10921).

Suitable strong acids are, for example, mineral acids, such as $H_2SO_4$ or HCl, or strong organic acids, such as trifluoroacetic acid. The tert-butyl protective group is deaved off, for example, at temperatures of from -20° C. to the respective reflux temperature of the reaction mixture, preferably at from 0° C. to 40° C. The reaction can be carried out neat or else in an inert solvent, such as, for example, dichloromethane or trichloromethane.

The compounds of the formula (VIII) are obtained, for example, from suitable amine precursors of the formula (IX) by diazotization and subsequent coupling of the resulting diazonium salts with CH-acidic compounds of the formula (X) (cf. in this context: Houben-Weyl, "Methoden der organischen Chemie", 4th ed., Vol. 10/3, p. 490 ff),

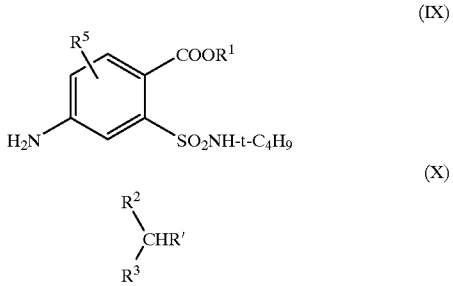

in which R' is H, $CO_2H$, $COCH_3$, $CO_2Me$ or $CO_2Et$.

In some cases, it is possible to carry out further derivatizations by methods known from the literature to introduce radicals $R^4 \neq$ H after the coupling with the CH-acidic compound, for example alkylations or acylations (cf. Houben-Weyl, "Methoden der organischen Chemie", 4th ed., Vol.10/2, p. 402 ff. and p. 385).

The abovementioned aniline derivatives of the formula (IX)areotaied by processes known from the literature by reduction of the corresponding nitro compounds (XI) (see below), for example by hydrogenation using hydrogen in the presence of a suitable catalyst, such as Pd-C or Raney nickel, or by reduction with iron in an acetic acid medium; cf. in this context: H. Berrie, G. T. Neuhold, F. S. Spring, J. Chem. Soc. (1952), 2042; M. Freifelder, "Catalytic Hydrogenation in Organic Synthesis: Procedures and Commentary", J. Wiley and Sons, New York (1978), chap. 5.

The aromatic sulfonamides of the formula (XI) can be obtained from the sulfonic acids of the formula (XII).

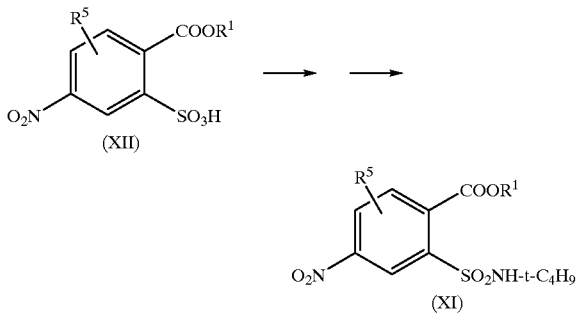

Initially, the suifonic acid group of the compounds (XII) is converted into the sulfochlorides, for example by standard methods such as reaction of phosphorus oxychloride or thionyl chloride with potassium salts of the corresponding sulfonic acids in inert solvents such as acetonitrie and/or sulfolane or net by heating at reflux (cf. Houben Weyl-Klamann, "Methoden der organishen Chemie", 4th ed., Vol. EX1/2p. 1067–1073 Thiem Verlag Stuttgart, 1985).

The sulfonamide fonatbion from the sulfochlorides using tert butylamine in ethanol or THF affords the compounds (XI) in good yields (cf. similar reacions in WO 89/10921).

The sulfonic acids of the formula (XII) can be prepared from the commercially available 2-methyl-5-nitrobenzenesulfonic acid. The substituent $COOR^1$ is introduced by oxidation of the methyl group of 2-methyl-5-nitrobenzenesulfonic acid by standard methods, such as for example, the reaction with potassium permananganate toge the carboxylic acid function, follomed by esterification. (cf. in this context: Houben-Weyl-Falbe: "Methoden der organischen Chemie", 4th ed., Vol. E V/1, Thieme Verlag Stuttgart, 1985, p. 199–202).

Alteratisvely, the intermfediates of the formula (XI) can also be obtained starting from the commercally avallable 2-amino-5-nitrobenzoic acid according to the following reaction scheme

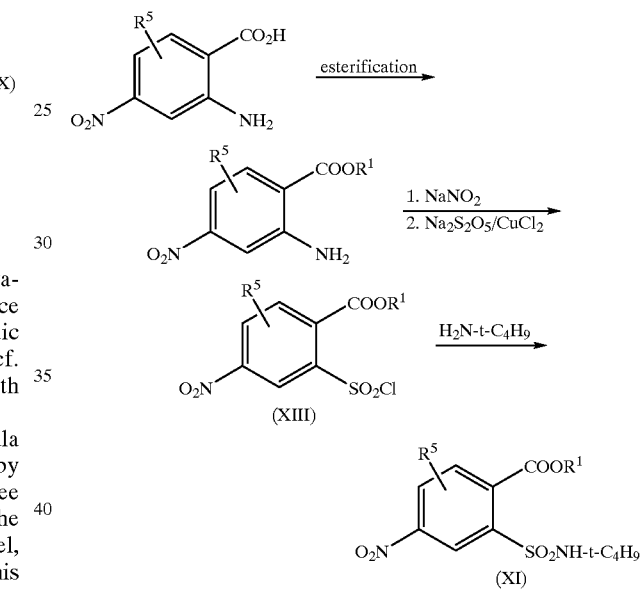

where all reaction steps can be carried out similar to methods known from the literature.

In a similar manner, the compounds of the formula (II) can also be prepared, avoiding the t-butyi protective group (cf. EP 562 575). For this a compound of the formula (XIII) is reached with ammonia instead of t-butylamlne, and the synthesis is continued as described for compound (XI) or in EP 562 575.

The carbamates of the formula (III) can be prepared by methods described in the South African Patent Applicatons 82/5671 and 82/5045 or EP-A 70804 (U.S. Pat. No. 4,480, 101) or RD 275056.

The reaction of the compounds (IV) with the aminoheterocycles (V) is preferably carried out in inert aprotic solvents, such as for example dioxane, acetonitrile or tetrahydrofuran, at temperature between 0° C. and the boiling temperature of the solvent. The required starting materials (V) are known from the literature or can be prepared by methods known from the literature. The phenylsulfonylcarbamates of the formula (IV) are obtained analogously to U.S. Pat. No. 4,684,393 or U.S. Pat No. 4,743,290.

The phenylsulfonylsocyanates of the fonrmla (VI) can be prepared analogously to U.S. Pat. No. 4,481,029 and reacted withe aminoheterocydes (V).

The (thio)isocyanates of the formula (VII) are obtainable by methods known from the literature (EP-A-232067, EP-A-166516). The reaction of the (thio)isocyanates (VII) with compounds (II) is carried out at from −10° C. to 100° C., preferably at from 20 to 100° C., in an inert a protic solvent, such as, for example, acetone or acetonitrile, in the presence of a suitable base, for example $N(C_2H_5)_3$ or $K_2CO_3$.

The reaction of an aminoheterocyde of the formula (V) with diphenyl carbonate and a sulfonamide of the formula (II) can be carried out in a one-pot reaction in accordance with EP-A-562 575.

The salts of the compounds of the formula (I) are preferably prepared in inert polar solvents, such as, for example, water, methanol or acetone, at temperatures of 0–100° C. Bases which are suitable for preparing the salts according to the Invention are for example, alkali metal carbonates, such as potassium carbonate, alkali metal and alkaline earth metal hydroxides, for example NaOH or KOH, or ammonia or ethanolamine.

Solvents which have been termed "inert solvents" in the above process variants are to be understood as meaning in each case solvents which are inert under the prevailing reaction conditions, but which do not have to be inert under any selected reaction conditions.

The compounds of the formula (I) and salts thereof according to the invention, hereinbelow together refered to as compounds of the formula (I) (according to the invention), have an outstanding herbicidal activity against a broad spectrum of economically important monocotyledonous and dicotyledonous harmful plants. The active substances also act efficiently on perennial broad-leaved weeds which produce shoots from rhizomes, rootstocks or other perennial organs and which are difficult to control. In this context, It does not matter whether the substance are applied before sowing, pre-emergence or post-emergence.

Specfically, examples may be mentioned of some representatives of the monocotyledonous and dicotyledonous weed flora which can be controlled by the compounds according to the invention, without the enumeration being a restriction to certain species.

Examples of weed species on which the active substance acts efficienty are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the activity spectrum extends to species such as, for example, Galium, Viola, Veronica, Larmium, Stellaria, Amaranthus, Sinapis, ipomoea, Matricaria, Abutilon and Sida from amongst the annuals, and Convolvulus, Cirsium, Rumex and Artemisia in the case of the perennial weeds.

The active substances according to the invention also effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage, but then their gmwh stops, and, eventually after three to four weeks have elapse, they die completely.

If the active substances are applied post-emergence to the green parts of the plants, growth likewise stops drastically a very short time after the treatment and the weed plants remain at the growth staget of the point of time of application, or they die completely after a certain time, so that In this manner, competition by the weeds, which is harnful to the crop plants, is eliminated at a very early point in time and in a sustained manner.

Even though the compounds according to the invention have an excellent herbicidal activity against monocotyledonous and dicotyledonous weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in areas of agricultural crops.

In addition, the substances according to the invention have outstanding growth-regulatory properties in crop plants. They engage in the plant metabolism in a regulating manner and can thus be employed for the targeted control of plant constituents and for facilitating harvesting, for example by triggering desiccation and stunted growth. Moreover, they are also suitable for the general control and inhibition of undesirable vegetative growth without destroying the plants in the process. The inhibition of vegetative growth is very important in a large number of monocotyledonous and dicotyledonous crops since t can reduce, or completely prevent, lodging.

The compounds according to the invention can be applied in the form of wettable powders, emulsifiable concentrates, sprayable solutions, dusts or granules in the customary preparations. The invention therefore also relates to herbicidal and plant-growth-regulating compositions which comprise the compounds of the formula (I).

The compounds of the formula (I) can be formulated in various ways, depending on the prevailing biological and/or chemico-physical parameters. The following possibilities are suitable formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hauser Veriag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encydopedia of Surface Active Agents", Chem. Publ. Co. Inc., N.Y. 1964; Schönfeldt, "Grenzflächenakfive Äthylenoxidaddukte" [Surfaceactive ethylene oxide adducts], Wiss. Verlagsgesell., Stuttgart 1976; Winnacker-Küchler, "Chemische Technolie" [Chemical Technology], Volume 7, C. Hauser Verlag Munich, 4th Ed. 1986.

Based on these formulations, it is also possible to prepare combinations with other pesticidally active substances, such as, for example, insecticides, acaricides, herbicides, fungicides, and also with safeners, fertlizers and/or growth regulators, for example in the form of a ready mix or a tank mix.

Wettable powders are preparations which are uniformly dispersible in water and which, besides the active substance, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disutfonate, sodium dibutylnaphthalene-sulfonate or else sodium oleoylmethyltaurinate, in addition to a diluent or inert substance. To prepare the wettable powders, the herbicidally active substances are ground finely, for example in customary equipment such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene, or else higher-boiling aromatics or hydrocarbons or mixtures of the organic solvents with the addition of one or more ionic andlor nonionic surfactants (emulsifiers). Examples of emulsifiers which can be used are: calcium salts of alkylarylsulfonIc acids such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely divided solid substances, for example talc, natural days such as kaolin, bentonite and pyrophyllite, or diatomaceous earth.

Suspension concentrates can be water- or oil-based. They can be prepared, for example, by wet grinding using commercially available bead mills with an optional addition of surfactants as already mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants as already mentioned above for example in the case of the other types of formulation.

Granules can be prepared either by spraying the active substance onto adsorptive granulated inert material or by applying active substance concentrates to the surface of carriers such as sand, kaolinites or of granulated inert material by means of binders, for example polyvinyl alcohol, sodium polyacrylate or else mineral oils. Suitable active substances can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fludized-bed, extruder and spray granules, see, for exampile, the processes in "Spray-Drying Handbook" 3rd ed. 1979, G. Goodwin Ltd., London; J. E. Browning. "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

In general, the agrochemical preparations comprise 0.1 to 99% by weight, in particular 0.1 to 95% by weight, of active substance of the formula (I). The active substance concentration in wettable powders is, for example, approximately 10 to 90% by weight, the remainder to 100% by weight being composed of customary formulation components. In the case of emulsifiable concentrates, the active substance concentrntton may amount to approximately 1 to 90, preferably 5 to 80%, by weight. Formulations in the form of dusts comprise 1 to 30% by weight of active substance, in most cases preferably 5 to 20% by weight of active substance, and sprayable solutions comprise approximately 0.05 to 80, preferably 2 to 50%, by weight of active substance. The active substance content of water-dispersible granules depends partiy on whether the active compound is in liquid or solid form and on which granulation auxiliaries, fillers and the like are being used. The active substance content of the water-dispersible granules amounts to, for example, between 1 and 95% by weight, preferably between 10 and 80% by weight.

In addition, the abovementioned formulations of active substances comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

components which can be used in combination with the active substances according to the invention in mixed formulations or in the tank mix are, for example, known active subnces as they are described, for example, in Weed Research 26, 441–445 (1986), or "The Pesticide Manual", 10th edition, The British Crop Protecion Council and the Royal Soc. of Chemistry, 1994, and the literature cited therein. Examples of active substances which may be mentioned as herbicides which are known from the literature and which can be combined with the compounds of the formula (I) are the followng (note: either the common names in accordance with the Intenational Organization for Standardization (ISO) or the chemical names, if appropriate together with a customary code number, of the compounds are given): acetochlor acifluorfen; aclonifen; AKH 7088, i.e. [[[1-[5-[2-chloro-4-(trifluoromethyl)phenoxy]-2-nitrophenyl]-2-methoxyethylidene]amino]oxy]-acetic acid and its methyl ester, alachlor; alloxydim; ametryn; amidosulfuron; amitrol; AMS, i.e. ammonium sulfamate; anilofos; asulam; atrazine; azimsulfurone (DPX-A8947); aziprotryn; barban BAS 516 H, i.e. 5-fluoro-2-pheyl-4H-3,1-benzoxazin-4-one; benazolin; benfluralin; benfuresate; bensuffuron-methyl; bensulide; bentazone; benzofenap; benzofluor; benzoylprop-ethyl; bernzthiazuron; bialaphos; bifenox; bromacil; bromobutide; bromofenoxim; bromoxynil; bromuron; buminafos; busoxinone; butachlor, butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940) cyanazine; cycloate; cyclosulfamuron (AC 104); cycloxydim; cycluron; cyhalofop and its ester derivatives (for example butyl ester, DEH-112) cyperquat cyprazine; cyprazole; daimuron; 2,4-DB; dalapon; desmedipham; desmetryn; di-allate; dicamba; dichlobenil; dichlorprop; diclofop and its esters such as diclofop; methyl; diethatyl; difenzoquat; diflufenican; dimefuron; dimethachlor dimethametryn; dimethenamid (SAN-582H); dimethazone, clomazon; dimethipin; dimetrasulfuron; dinitramine; dinoseb; dinoterb; diphenamid; dipropetryn; diquat; dithlop; diuron; DNOC; eglinazine-ethyl; EL 77, i.e. 5-cyano-1-(1,1-dimethylethyl)-N-methyl-1H-pyrazole-4-carboxamide; pyrazole4-carboxamide; endothal; EPTC; espprocarb; ethalfluralin; ethametsulfuron-methyl; ethidimuron; ethofumesate; F5231, i.e. N-[2-chloro-4-fluoro-5-[4-(3-fluoropropyl)-4,5-dihydro-5-oxo1H-tetrazol-1-yl]phenyl]ethanesulfonamide; ethoxyfen and its esters (for example ethyl ester, HN-252); etobenzanid (HW 52); fenoprop, fenoxan, fenoxaprop and fenoxaprop-P and their esters, for example fenoxaprop-P-ethyl and fenoxaprop-ethyl; fenoxydim; fenuron; flamprop-methyl; flazasulfron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6chloro-N-(3chloro-2-propenyl)-5methly-N-phenyl-3-pyridazinamine; MT 5950, i.e. N-[3-chloro-4(1-methylethyl)phenyl]-2-methylpentanamide naproapilide; napropamide; naptalam; NC 310, i.e. 4-(2,4-dichlorobenzoyl)-1-methyl-5-benzyloxypyrazole; neburon; niccosulfuron; nipyraclophen; nitralin; nitrofen; nitrofluorfen; norflurazon; orbencarb; oryzalin; oxadiargyl (RP-020630); oxadiazon, oxyfluorfen; parquat; pebulate, pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon;, prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyaosulfuron-ethyl; pyrazoxyfen; pyridate; pyrithiobac (KIH-2031); pyroxofop and its esters(for example propargyl ester); quinclorac; quinmerac; quinofop and its ester deratives, quizalofop and quizalofop-P and their ester derivatves for example quizalofop-ethyl; quizalofop-P-tefuryl and -ethyl; renriduron; rimsulfuron (DPX-E 9636); S 275, i.e. 2-[4-chlor-2-fluoro-5-(2-propynyloxy)phenyl]4, 5,6,7-tetrahydro-2H-indazole, secbumeton; sethoxydim; siduron; simazine; simetryn; SN 106279, i.e. 2[[7-[2-chloro-4-(trifluoromethyl)phenoxy]-2-naphthalenyl]oxy]propanoic acid and its methyl ester; sulfentrazone (FMC-97285, F-6285); sulfazuron; sulfometuron-methyl; sulfosate (ICI-A0224); TCA; tebutam (GCP-5544); tebuthiuron; terbacil; terbucarb; terbuchlor, terbumeton; terbuthylazine; terbutryn; TFH 450, i.e. N,N-diethyl-3-[(2-ethyl-6-methylphenyl) sulfonyl]-1H-1,2,4-triazole-1-carboxamide; thenyichlor (NSK-850); thiazafluron; thiazopyr (Mon-13200); thidiazimine (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vemolate; WL 110547, i.e. 5-phenoxy-1-[3-(trifluoromethyl)phenyl]-1H-tetrazole; UBH-509; D-489; LS 82–556; KPP-300; NC-324; NC-330; KH-218; DPX-N8189; SC-0774; DOWCO-535; DK-8910; V-53482; PP-600; MBH-001; KIH-9201; ET-751; KIH6127 and KIH-2023.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are conventionally not diluted any further with inert substances prior to use.

The application rate required, of the compounds of the formula (I), varies with the external factors such as, inter alia, temperature, humidity and nature of the herbicide used. It can vary within wide limits, for example between 0.001 and 10.0 kg/ha or more of active substance, but it is preferably between 0.005 and 5 kg/ha.

A. CHEMICAL EXAMPLES

Example A1

Methyl 4-amino-2-(N-tert-butylsulfamoyl)benzoate 50.0 g (0.158 mol) of methyl 2-(N-tert-butylsulfamoyl)-4-nitrobenzoate (prepared according to DE-OS 4 236 902) are added to a mixture of 180 ml of acetic acid and 75 ml of water, and the mixture is heated to 80° C. 26.5 g (0.474 mol) of iron powder are added a little at a time in such a manner that the temperature does not rise above 85° C. The mixture is subsequently stirred at 80° C. for 4 h, 85 ml of 2N HCl are added at this temperature and the mixture is allowed to cool to 25° C. The mixture is filtered off and the solid is washed thoroughly with water. The solid is subsequently 3× extracted hot with in each case 250 ml of ethyl acetate. The ethyl acetate phase is evaporated, and the residue is triturated with diisopropyl ether and dried. This gives 37.7 g (83% of theory) of methyl 4-amino-2-(N-tert-butylsulfamoyl)benzoate of m.p. 198–1990° C.

Example A2

Methyl 2-(N-tert-butylsulfamoyl)-4-(ethoxycarbonyl-nitromethylenehydrazino)benzoate 5.7 g (0.02 mol) of methyl 4-amino-2-(N-tert-butylsulfamoyl)benzoate are suspended in a mixture of 30 ml of conc. HCl and 36 ml of water. At 0–50° C., a solution of 1.5 g (0.022 mol) of sodium nitrite in 9 ml of water is added dropwise. The few undissolved components are filtered off cold, and the cold diazonium salt solution is slowly poured, at 5–10° C., into a mixture of 8.9 g (0.11 mol) of sodium acetate, 16 ml of water, 60 ml of ethanol and 2.7 g (0.02 mol) of ethyl nitroacetate. Stirring is continued at 0° C. for 2 h and the mixture is left to stand at this temperature for 15 h. The mixture is filtered off and the solid is washed with water and dried under reduced pressure, giving 5.2 g (60% of theory) of methyl 2-(N-tert-butylsulfamoyl)-4-(ethoxycarbonylnitromethylenehydrazino)benzoate of m.p. 142–145° C.

Example A3

Methyl 2-(N-tert-butylsulfamoyl)-4-(cyano-ethoxycarbonylmethylene-hydrazino)benzoate 4.3 g (15 mmol) of methyl 4-amino-2-(N-tert-butylsulfamoyl)benzoate are suspended in a mixture of 22 ml of conc. HCl and 27 ml of water. At 0–5° C., a solution of 1.1 g (16.5 mmol) of sodium nitrite in 7 ml of water is added dropwise. After 10 min, the few undissolved components are filtered off cold and the cold diazonium salt solution is, at 5–10° C., added dropwise to a mixture of 6.7 g (81 mmol) of sodium acetate, 12 ml of water, 45 ml of ethanol and 1.7 g (15 mmol) of ethyl cyanoacetate. The mixture is stirred at 0° C. for another 2 h and then left to stand at this temperature for 15 h. The mixture is filtered off and the solid is washed with water and dried under reduced pressure, giving 2.0 g (33% of theory) of methyl 2-(N-tert-butylsulfamoyl)A-(cyanoethoxycarbonylmethylenehydrazino)benzoate of m.p. 162° C.

Example A4

Methyl 4-(cyanoethoxycarbonylmethylenehydrazino)-2-sulfamoylbenzoate

At 0–5° C., 2.5 g (6 mmol) of methyl 2-(N-tert-butylsulfamoyl)-4-(cyano-ethoxycarbonylmethylidenehydrazino)benzoate in 30 ml of trifluoroacetic acid are stirred for 1.5 h. The mixture is concentrated and the residue is triturated with diethyl ether. The mixture is filtered off with suction and dried, giving 2.0 g (92% of theory) of methyl 4-(cyanoethoxycarbonyl-methylenehydrazino)-2-sulfamoylbenzoate of m.p. 188–189° C.

Example A5

Methyl 4-(cyanoethoxycarbonylmethylidenehydrazino)-2-[3-(4,6-dimethoxypyrimidin-2-yl)ureidosulfonyl]benzoate, sodium salt At 0° C., 0,14 g (3.5 mmol) of powdered sodium hydroxide are added to a mixture of 1.0 g (2.8 mmol) of methyl 4-(cyanoethoxycarbonylmethylidene-hydrazino)-2-sulfamoylbenzoate, 0.9 g (3.4 mmol) of phenyl N-(4,6-dimethoxypyrimidin-2-yl)carbamate and 22 ml of acetonitrile. The mixture is stirred at 0° C. for 2 hours and then filtered off. The solid is washed with a little diethyl ether and dried. This gives 1.3 g (83% of theory) of methyl 4-(cyanoethoxycarbonylmethylenehydrazino)2-[3-(4,6dimethoxypyrimidin-2-yl)ureidosulfonyl]benzoate as the sodium salt of m.p. 256–258° C. (decomp.).

Example A6

Methyl 4(cyanoethoxycarbonylmethylidenehydrazino)2-[3-(4, 6-dimethoxypyrimidin-2-yl)ureidosulfonyl]benzoate 0.7 g (1.25 mmol) of methyl 4-(cyanoethoxycarbonylmethylhydrazino)-2-[3-(4,6-dimethoxypyrimidin-2-yl)ureidosulfonyl]benzoate, sodium salt, are dissolved in 15 ml of water. The few undissolved components are filtered off and the filtrate is acidified to pH 1 using 2N hydrochloric acid. The precipitated solid is filtered off with suction, washed with water and dried. This gives 0.5 g (75% of theory) of methyl 4-(cyanoethoxycarbonyl-methyldenhydrazino)-2-[3-(4,6-dimethoxypyrimidin-2-yl) ureidosulfonyl]benzoate of m.p. 145° C. (decomp.)

The compounds described in Table 1 below are obtained in accordance with or similar to the Examples A1 to A6 above.

| Abbreviations in the table: | |
|---|---|
| m.p. = | melting point in ° C. |
| (decomp.) = | melting point with decomposition |
| Ac = | acetyl |
| Bu = | $^n$Bu = n-butyl |
| Et = | ethyl |
| Me = | methyl |
| Ph = | phenyl |
| Pr = | $^n$Pr = n-propyl |
| i-Pr = | isopropyl |
| Het = | heterocycle, where Het represents one of the radicals T1 to T15 |

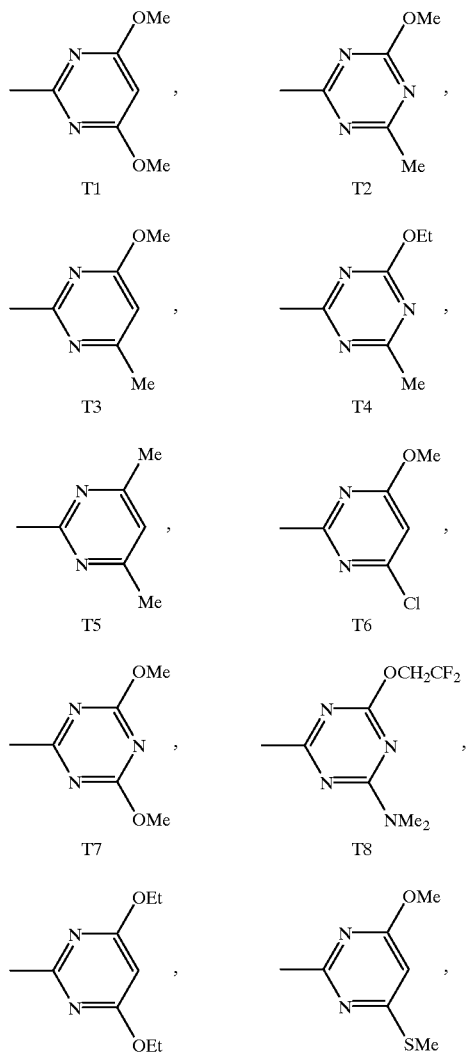

-continued

Abbreviations in the table:

T9, T10

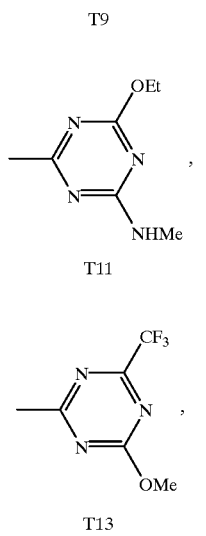

T11, T12

T13, T14

-continued

Abbreviations in the table:

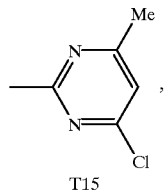

T15

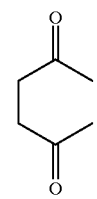

A diradical such as in the columns $R^2$, $R^3$ means that $R^2$ and $R^3$ together represent the diradical bridge and together with the carbon atom of the group $R^2R^3C$ form an alkylidene radical. This applies correspondingly to other enties made for two columns.

TABLE 1

Compounds of the formula (1)

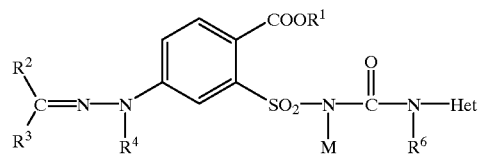

(1)

| Ex. No. | $R^1$ | $R^2$ | $R^3$ | $R^4$ | $R^6$ | M | Het | m.p. |
|---|---|---|---|---|---|---|---|---|
| 1 | Me | COMe | COOMe | H | H | H | T1 | |
| 2 | Me | COMe | COOMe | H | H | Na | T1 | |
| 3 | Me | COMe | COOMe | H | H | H | T2 | |
| 4 | Me | COMe | COOMe | H | H | Na | T2 | |
| 5 | Me | COMe | COOEt | H | H | H | T1 | 132–133 (decomp.) |
| 6 | Me | COMe | COOEt | H | H | Na | T1 | 209–211 (decomp.) |
| 7 | Me | COMe | COOEt | H | H | H | T2 | |
| 8 | Me | COMe | COOEt | H | H | Na | T2 | |
| 9 | Me | COEt | COOMe | H | H | H | T1 | |
| 10 | Me | COEt | COOMe | H | H | Na | T1 | |
| 11 | Me | COEt | COOMe | H | H | H | T2 | |
| 12 | Me | COEt | COOMe | H | H | Na | T2 | |
| 13 | Me | COBu | COOMe | H | H | H | T1 | |
| 14 | Me | COBu | COOMe | H | H | Na | T1 | |
| 15 | Me | COBu | COOMe | H | H | H | T2 | |
| 16 | Me | COBu | COOMe | H | H | Na | T2 | |
| 17 | Me | COMe | COMe | H | H | H | T1 | 137–141 (decomp.) |
| 18 | Me | COMe | COMe | H | H | Na | T1 | 186–189 (decomp.) |
| 19 | Me | COMe | COMe | H | H | H | T2 | |
| 20 | Me | COMe | COMe | H | H | Na | T2 | |
| 21 | Me | COMe | H | H | H | H | T1 | |
| 22 | Me | COMe | H | H | H | Na | T1 | |
| 23 | Me | COMe | H | H | H | H | T2 | |
| 24 | Me | COMe | H | H | H | Na | T2 | |
| 25 | Me | COMe | Me | H | H | H | T1 | |
| 26 | Me | COMe | Me | H | H | Na | T1 | |
| 27 | Me | COMe | Me | H | H | H | T2 | |
| 28 | Me | COMe | Me | H | H | Na | T2 | |
| 29 | Me | COMe | Bu | H | H | H | T1 | |

TABLE 1-continued

Compounds of the formula (1)

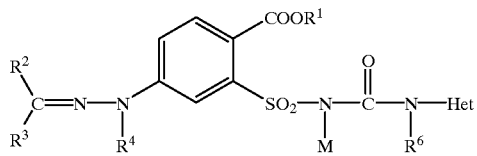

(1)

| Ex. No. | R¹ | R² | R³ | R⁴ | R⁶ | M | Het | m.p. |
|---|---|---|---|---|---|---|---|---|
| 30 | Me | COMe | Bu | H | H | Na | T1 | |
| 31 | Me | COMe | Bu | H | H | H | T2 | |
| 32 | Me | COMe | Bu | H | H | Na | T2 | |
| 33 | Me | COMe | CONH₂ | H | H | H | T1 | |
| 34 | Me | COMe | CONH₂ | H | H | Na | T1 | |
| 35 | Me | COMe | CONEt₂ | H | H | H | T1 | |
| 36 | Me | COMe | CONH₂ | H | H | H | T2 | |
| 37 | Me | COMe | CONH₂ | H | H | Na | T2 | |
| 38 | Me | COMe | CONHMe | H | H | H | T1 | |
| 39 | Me | COMe | CONHMe | H | H | Na | T1 | |
| 40 | Me | COMe | CONHMe | H | H | H | T2 | |
| 41 | Me | COMe | CONHMe | H | H | Na | T2 | |
| 42 | Me | COMe | CONHPh | H | H | H | T1 | 186–189 (decomp.) |
| 43 | Me | COMe | CONHPh | H | H | Na | T1 | 239–243 (decomp.) |
| 44 | Me | COMe | CONHPh | H | H | H | T2 | |
| 45 | Me | COMe | CONHPh | H | H | Na | T2 | |
| 46 | Me | COMe | CONMe₂ | H | H | H | T1 | 226–228 (decomp.) |
| 47 | Me | COMe | CONMe₂ | H | H | Na | T1 | 246–249 (decomp.) |
| 48 | Me | COMe | CONMe₂ | H | H | H | T2 | |
| 49 | Me | COMe | CONMe₂ | H | H | Na | T2 | |
| 50 | Me | CHO | COOMe | H | H | H | T1 | |
| 51 | Me | CHO | COOMe | H | H | Na | T1 | |
| 52 | Me | CHO | COOMe | H | H | H | T2 | |
| 53 | Me | CHO | COOMe | H | H | Na | T2 | |
| 54 | Me | COPh | COOMe | H | H | H | T1 | |
| 55 | Me | COPh | COOMe | H | H | Na | T1 | |
| 56 | Me | COPh | COOMe | H | H | H | T2 | |
| 57 | Me | COPh | COOMe | H | H | Na | T2 | |
| 58 | Me | COOMe | COOMe | H | H | H | T1 | 201–204 (decomp.) |
| 59 | Me | COOMe | COOMe | H | H | Na | T1 | 266–269 (decomp.) |
| 60 | Me | COOMe | COOMe | H | H | H | T2 | |
| 61 | Me | COOMe | COOMe | H | H | Na | T2 | |
| 62 | Me | COOMe | COOMe | H | H | H | T5 | |
| 63 | Me | COOMe | COOMe | H | H | Na | T5 | |
| 64 | Me | COOMe | COOMe | H | H | H | T6 | |
| 65 | Me | COOMe | COOMe | H | H | Na | T6 | |
| 66 | Me | COOEt | COOEt | H | H | H | T1 | |
| 67 | Me | COOEt | COOEt | H | H | Na | T1 | 109–111 (decomp.) |
| 68 | Me | COOEt | COOEt | H | H | H | T2 | |
| 69 | Me | COOEt | COOEt | H | H | Na | T2 | |
| 70 | Me | COOEt | COOEt | H | H | H | T5 | |
| 71 | Me | COOEt | COOEt | H | H | Na | T5 | |
| 72 | Me | COOEt | COOEt | H | H | H | T6 | |
| 73 | Me | COOEt | COOEt | H | H | Na | T6 | |
| 74 | Me | COOMe | CN | H | H | H | T1 | 148–152 (decomp.) |
| 75 | Me | COOMe | CN | H | H | Na | T1 | 238–243 (decomp.) |
| 76 | Me | COOMe | CN | H | H | K | T1 | |
| 77 | Me | COOMe | CN | H | H | NH₄ | T1 | |
| 78 | Me | COOMe | CN | H | H | NMe₄ | T1 | |
| 79 | Me | COOMe | CN | H | H | NHEt₃ | T1 | |
| 80 | Me | COOMe | CN | H | H | H | T2 | |
| 81 | Me | COOMe | CN | H | H | Na | T2 | |
| 82 | Me | COOMe | CN | H | H | K | T2 | |
| 83 | Me | COOMe | CN | H | H | NH₄ | T2 | |
| 84 | Me | COOMe | CN | H | H | NMe₄ | T2 | |
| 85 | Me | COOMe | CN | H | H | NHEt₄ | T2 | |
| 86 | Me | COOMe | CN | H | H | H | T3 | |
| 87 | Me | COOMe | CN | H | H | Na | T3 | |
| 88 | Me | COOMe | CN | H | H | H | T4 | |
| 89 | Me | COOMe | CN | H | H | Na | T4 | |
| 90 | Me | COOMe | CN | H | H | H | T5 | |
| 91 | Me | COOMe | CN | H | H | Na | T5 | |
| 92 | Me | COOMe | CN | H | H | H | T6 | |
| 93 | Me | COOMe | CN | H | H | Na | T6 | |

TABLE 1-continued

Compounds of the formula (1)

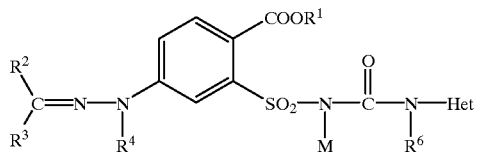

(1)

| Ex. No. | R¹ | R² | R³ | R⁴ | R⁶ | M | Het | m.p. |
|---|---|---|---|---|---|---|---|---|
| 94 | Me | COOMe | CN | H | H | H | T7 | |
| 95 | Me | COOMe | CN | H | H | Na | T7 | |
| 96 | Me | COOMe | CN | H | H | H | T8 | |
| 97 | Me | COOMe | CN | H | H | Na | T8 | |
| 98 | Me | COOMe | CN | H | H | H | T9 | |
| 99 | Me | COOMe | CN | H | H | Na | T9 | |
| 100 | Me | COOMe | CN | H | H | H | T10 | |
| 101 | Me | COOMe | CN | H | H | Na | T10 | |
| 102 | Me | COOMe | CN | H | H | H | T11 | |
| 103 | Me | COOMe | CN | H | H | Na | T11 | |
| 104 | Me | COOMe | CN | H | H | H | T12 | |
| 105 | Me | COOMe | CN | H | H | Na | T12 | |
| 106 | Me | COOMe | CN | H | H | H | T13 | |
| 107 | Me | COOMe | CN | H | H | Na | T13 | |
| 108 | Me | COOMe | CN | H | H | H | T14 | |
| 109 | Me | COOMe | CN | H | H | Na | T14 | |
| 110 | Me | COOMe | CN | H | H | H | T15 | |
| 111 | Me | COOMe | CN | H | H | Na | T15 | |
| 112 | Me | COOEt | CN | H | H | H | T1 | 145 (decomp.) |
| 113 | Me | COOEt | CN | H | H | Na | T1 | 256–258 (decomp.) |
| 114 | Me | COOEt | CN | H | H | K | T1 | |
| 115 | Me | COOEt | CN | H | H | NH₄ | T1 | |
| 116 | Me | COOEt | CN | H | H | NMe₄ | T1 | |
| 117 | Me | COOEt | CN | H | H | NHEt₃ | T1 | |
| 118 | Me | COOEt | CN | H | H | H | T2 | |
| 119 | Me | COOEt | CN | H | H | Na | T2 | |
| 120 | Me | COOEt | CN | H | H | K | T2 | |
| 121 | Me | COOEt | CN | H | H | NH₄ | T2 | |
| 122 | Me | COOEt | CN | H | H | NMe₄ | T2 | |
| 123 | Me | COOEt | CN | H | H | NHEt₃ | T2 | |
| 124 | Me | COOEt | CN | H | H | H | T3 | |
| 125 | Me | COOEt | CN | H | H | Na | T3 | |
| 126 | Me | COOEt | CN | H | H | H | T4 | |
| 127 | Me | COOEt | CN | H | H | Na | T4 | |
| 128 | Me | COOEt | CN | H | H | H | T5 | |
| 129 | Me | COOEt | CN | H | H | Na | T5 | |
| 130 | Me | COOEt | CN | H | H | H | T6 | |
| 131 | Me | COOEt | CN | H | H | Na | T6 | |
| 132 | Me | COOEt | CN | H | H | H | T7 | |
| 133 | Me | COOEt | CN | H | H | Na | T7 | |
| 134 | Me | COOEt | CN | H | H | H | T8 | |
| 135 | Me | COOEt | CN | H | H | Na | T8 | |
| 136 | Me | COOEt | CN | H | H | H | T9 | |
| 137 | Me | COOEt | CN | H | H | Na | T9 | |
| 138 | Me | COOEt | CN | H | H | H | T10 | |
| 139 | Me | COOEt | CN | H | H | Na | T10 | |
| 140 | Me | COOEt | CN | H | H | H | T11 | |
| 141 | Me | COOEt | CN | H | H | Na | T11 | |
| 142 | Me | COOEt | CN | H | H | H | T12 | |
| 143 | Me | COOEt | CN | H | H | Na | T12 | |
| 144 | Me | COOEt | CN | H | H | H | T13 | |
| 145 | Me | COOEt | CN | H | H | Na | T13 | |
| 146 | Me | COOEt | CN | H | H | H | T14 | |
| 147 | Me | COOEt | CN | H | H | Na | T14 | |
| 148 | Me | COOEt | CN | H | H | H | T15 | |
| 149 | Me | COOEt | CN | H | H | Na | T15 | |
| 150 | Me | COOEt | NO₂ | H | H | H | T1 | 138–140 (decomp.) |
| 151 | Me | COOEt | NO₂ | Na | H | Na | T1 | 280 (decomp.) |
| 152 | Me | COOEt | NO₂ | H | H | H | T2 | |
| 153 | Me | COOEt | NO₂ | H | H | Na | T2 | |
| 154 | Me | COOEt | NO₂ | H | H | H | T5 | |
| 155 | Me | COOEt | NO₂ | H | H | Na | T5 | |
| 156 | Me | COOEt | NO₂ | H | H | H | T6 | |
| 157 | Me | COOEt | NO₂ | H | H | Na | T6 | |

TABLE 1-continued

Compounds of the formula (1)

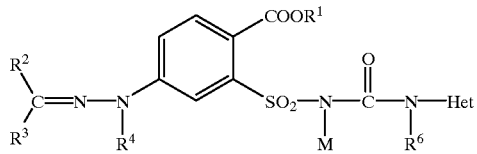

(1)

| Ex. No. | R¹ | R² | R³ | R⁴ | R⁶ | M | Het | m.p. |
|---|---|---|---|---|---|---|---|---|
| 158 | Me | COOEt | CF₃ | H | H | H | T1 | |
| 159 | Me | COOEt | CF₃ | H | H | Na | T1 | |
| 160 | Me | COOEt | CF₃ | H | H | H | T2 | |
| 161 | Me | COOEt | CF₃ | H | H | Na | T2 | |
| 162 | Me | COOEt | CF₃ | H | H | H | T5 | |
| 163 | Me | COOEt | CF₃ | H | H | Na | T5 | |
| 164 | Me | COOEt | CF₃ | H | H | H | T6 | |
| 165 | Me | COOEt | CF₃ | H | H | Na | T6 | |
| 166 | Me | COOEt | SO₂Me | H | H | H | T1 | 181–184 (decomp.) |
| 167 | Me | COOEt | SO₂Me | H | H | Na | T1 | |
| 168 | Me | COOEt | SO₂Me | H | H | H | T2 | |
| 169 | Me | COOEt | SO₂Me | H | H | Na | T2 | |
| 170 | Me | COOEt | SO₂Me | H | H | H | T5 | |
| 171 | Me | COOEt | SO₂Me | H | H | Na | T5 | |
| 172 | Me | COOEt | SO₂Me | H | H | H | T6 | |
| 173 | Me | COOEt | SO₂Me | H | H | Na | T6 | |
| 174 | Me | COOMe | SO₂Et | H | H | H | T1 | |
| 175 | Me | COOMe | SO₂Et | H | H | Na | T1 | |
| 176 | Me | COOMe | SO₂Et | H | H | H | T2 | |
| 177 | Me | COOMe | SO₂Et | H | H | Na | T2 | |
| 178 | Me | COOMe | SO₂Me | H | H | H | T1 | |
| 179 | Me | COOMe | SO₂Me | H | H | Na | T1 | |
| 180 | Me | COOMe | SO₂Me | H | H | H | T2 | |
| 181 | Me | COOMe | SO₂Me | H | H | Na | T2 | |
| 182 | Me | COOEt | PO(OEt)₂ | H | H | H | T1 | |
| 183 | Me | COOEt | PO(OEt)₂ | H | H | Na | T1 | |
| 184 | Me | COOEt | PO(OEt)₂ | H | H | H | T2 | |
| 185 | Me | COOEt | PO(OEt)₂ | H | H | Na | T2 | |
| 186 | Me | COOEt | CONH₂ | H | H | H | T1 | 163–164 (decomp.) |
| 187 | Me | COOEt | CONH₂ | H | H | Na | T1 | 189–191 (decomp.) |
| 188 | Me | COOEt | CONH₂ | H | H | H | T2 | |
| 189 | Me | COOEt | CONH₂ | H | H | Na | T2 | |
| 190 | Me | COOMe | Ph | H | H | H | T1 | |
| 191 | Me | COOMe | Ph | H | H | Na | T1 | |
| 192 | Me | COOMe | Ph | H | H | H | T2 | |
| 193 | Me | COOMe | Ph | H | H | Na | T2 | |
| 194 | Me | COOMe | Ph | H | H | H | T5 | |
| 195 | Me | COOMe | Ph | H | H | Na | T5 | |
| 196 | Me | COOMe | Ph | H | H | H | T6 | |
| 197 | Me | COOMe | Ph | H | H | Na | T6 | |
| 198 | Me | CONH₂ | CONH₂ | H | H | H | T1 | 179–182 (decomp.) |
| 199 | Me | CONH₂ | CONH₂ | H | H | Na | T1 | |
| 200 | Me | CONH₂ | CONH₂ | H | H | H | T2 | |
| 201 | Me | CONH₂ | CONH₂ | H | H | Na | T2 | |
| 202 | Me | CONMe₂ | CONMe₂ | H | H | H | T1 | |
| 203 | Me | CONMe₂ | CONMe₂ | H | H | Na | T1 | |
| 204 | Me | CONMe₂ | CONMe₂ | H | H | H | T2 | |
| 205 | Me | CONMe₂ | CONM 2 | H | H | Na | T2 | |
| 206 | Me | CONH₂ | CN | H | H | H | T1 | |
| 207 | Me | CONH₂ | CN | H | H | Na | T1 | |
| 208 | Me | CONH₂ | CN | H | H | H | T2 | |
| 209 | Me | CONH₂ | CN | H | H | Na | T2 | |
| 210 | Me | CN | SO₂Me | H | H | H | T1 | |
| 211 | Me | CN | SO₂Me | H | H | Na | T1 | |
| 212 | Me | CN | SO₂Me | H | H | H | T2 | |
| 213 | Me | CN | SO₂Me | H | H | Na | T2 | |
| 214 | Me | CN | CN | H | H | H | T1 | |
| 215 | Me | CN | CN | H | H | Na | T1 | 217–221 (decomp.) |
| 216 | Me | CN | CN | H | H | H | T2 | |
| 217 | Me | CN | CN | H | H | Na | T2 | |
| 218 | Me | CN | CN | H | H | H | T5 | |
| 219 | Me | CN | CN | H | H | Na | T5 | |
| 220 | Me | CN | CN | H | H | H | T6 | |
| 221 | Me | CN | CN | H | H | Na | T6 | |

TABLE 1-continued

Compounds of the formula (1)

| Ex. No. | R¹ | R² | R³ | R⁴ | R⁶ | M | Het | m.p. |
|---|---|---|---|---|---|---|---|---|
| 222 | Me | CN | Ph | H | H | H | T1 | |
| 223 | Me | CN | Ph | H | H | Na | T1 | |
| 224 | Me | CN | Ph | H | H | H | T2 | |
| 225 | Me | CN | Ph | H | H | Na | T2 | |
| 226 | Me | CN | Ph | H | H | H | T5 | |
| 227 | Me | CN | Ph | H | H | Na | T5 | |
| 228 | Me | CN | Ph | H | H | H | T6 | |
| 229 | Me | CN | Ph | H | H | Na | T6 | |
| 230 | Me | NO₂ | H | H | H | H | T1 | |
| 231 | Me | NO₂ | H | H | H | Na | T1 | |
| 232 | Me | NO₂ | H | H | H | H | T2 | |
| 233 | Me | NO₂ | H | H | H | Na | T2 | |
| 234 | Me | NO₂ | Me | H | H | H | T1 | |
| 235 | Me | NO₂ | Me | H | H | Na | T1 | |
| 236 | Me | NO₂ | Me | H | H | H | T2 | |
| 237 | Me | NO₂ | Me | H | H | Na | T2 | |
| 238 | Me | NO₂ | Bu | H | H | H | T1 | |
| 239 | Me | NO₂ | Bu | H | H | Na | T1 | |
| 240 | Me | NO₂ | Bu | H | H | H | T2 | |
| 241 | Me | NO₂ | Bu | H | H | Na | T2 | |
| 242 | Et | COOMe | CN | H | H | H | T1 | |
| 243 | Et | COOMe | CN | H | H | Na | T1 | |
| 244 | Et | COOMe | CN | H | H | H | T2 | |
| 245 | Et | COOMe | CN | H | H | Na | T2 | |
| 246 | Et | COOMe | CN | H | H | H | T5 | |
| 247 | Et | COOMe | CN | H | H | Na | T5 | |
| 248 | Et | COOMe | CN | H | H | H | T6 | |
| 249 | Et | COOMe | CN | H | H | Na | T6 | |
| 250 | Et | COOMe | CN | H | H | H | T1 | |
| 251 | Et | COOMe | CN | H | H | Na | T1 | |
| 252 | Et | COOMe | CN | H | H | H | T2 | |
| 253 | Et | COOMe | CN | H | H | Na | T2 | |
| 254 | Et | COOMe | NO₂ | H | H | H | T1 | |
| 255 | Et | COOMe | NO₂ | H | H | Na | T1 | |
| 256 | Et | COOMe | NO₂ | H | H | H | T2 | |
| 257 | Et | COOMe | NO₂ | H | H | Na | T2 | |
| 258 | Et | COOMe | COOMe | H | H | H | T1 | |
| 259 | Et | COOMe | COOMe | H | H | Na | T1 | |
| 260 | Et | COOMe | COOMe | H | H | H | T2 | |
| 261 | Et | COOMe | COOMe | H | H | Na | T2 | |
| 262 | i-Pr | COOMe | CN | H | H | H | T1 | |
| 263 | i-Pr | COOMe | CN | H | H | Na | T1 | |
| 264 | i-Pr | COOMe | CN | H | H | H | T2 | |
| 265 | i-Pr | COOMe | CN | H | H | Na | T2 | |
| 266 | 3-Oxetanyl | COOMe | CN | H | H | H | T1 | |
| 267 | 3-Oxetanyl | COOMe | CN | H | H | Na | T1 | |
| 268 | 3-Oxetanyl | COOMe | CN | H | H | H | T2 | |
| 269 | 3-Oxetanyl | COOMe | CN | H | H | Na | T2 | |
| 270 | 3-Oxetanyl | COOEt | CN | H | H | H | T1 | |
| 271 | 3-Oxetanyl | COOEt | CN | H | H | Na | T1 | |
| 272 | 3-Oxetanyl | COOEt | CN | H | H | H | T2 | |
| 273 | 3-Oxetanyl | COOEt | CN | H | H | Na | T2 | |
| 274 | 3-Oxetanyl | COOEt | NO₂ | H | H | H | T1 | |
| 275 | 3-Oxetanyl | COOEt | NO₂ | H | H | Na | T1 | |
| 276 | 3-Oxetanyl | COOEt | NO₂ | H | H | H | T2 | |
| 277 | 3-Oxetanyl | COOEt | NO₂ | H | H | Na | T2 | |
| 278 | 3-Oxetanyl | CN | CN | H | H | H | T1 | |
| 279 | 3-Oxetanyl | CN | CN | H | H | Na | T1 | |
| 280 | 3-Oxetanyl | CN | CN | H | H | H | T2 | |
| 281 | 3-Oxetanyl | CN | CN | H | H | Na | T2 | |
| 282 | Me | COOMe | CN | Me | H | H | T1 | |
| 283 | Me | COOMe | CN | Me | H | Na | T1 | |
| 284 | Me | COOMe | CN | Me | H | H | T2 | |
| 285 | Me | COOMe | CN | Me | H | Na | T2 | |

TABLE 1-continued

Compounds of the formula (1)

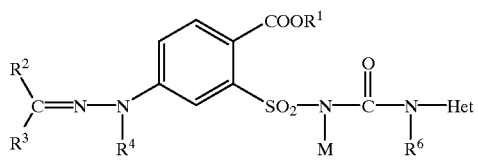

(1)

| Ex. No. | R¹ | R² | R³ | R⁴ | R⁶ | M | Het | m.p. |
|---|---|---|---|---|---|---|---|---|
| 286 | Me | COOEt | CN | COMe | H | H | T1 | |
| 287 | Me | COOEt | CN | COMe | H | Na | T1 | |
| 288 | Me | COOEt | CN | COMe | H | H | T2 | |
| 289 | Me | COOEt | CN | COMe | H | Na | T2 | |
| 290 | Me | COOMe | NO₂ | H | Me | H | T1 | |
| 291 | Me | COOMe | NO₂ | H | Me | Na | T1 | |
| 292 | Me | COOMe | NO₂ | H | Me | H | T2 | |
| 293 | Me | COOMe | NO₂ | H | Me | Na | T2 | |
| 294 | Me | COOMe | CN | H | Me | H | T1 | |
| 295 | Me | COOMe | CN | H | Me | Na | T1 | |
| 296 | Me | COOMe | CN | H | Me | H | T2 | |
| 297 | Me | COOMe | CN | H | Me | Na | T2 | |
| 298 | Me | COOMe | COOMe | H | Me | H | T1 | |
| 299 | Me | COOMe | COOMe | H | Me | Na | T1 | |
| 300 | Me | COOMe | COOMe | H | Me | H | T2 | |
| 301 | Me | COOMe | COOMe | H | H | Na | T2 | |
| 302 | Me | (hexane-2,5-dione group) | | H | H | H | T1 | 107–111 (decomp.) |
| 303 | Me | " | | H | H | Na | T1 | 238–244 (decomp.) |
| 304 | Me | " | | H | H | H | T2 | |
| 305 | Me | " | | H | H | Na | T2 | |
| 306 | Me | (pent-2-ene-2,4-dione group) | | H | H | H | T1 | |
| 307 | Me | " | | H | H | Na | T1 | |
| 308 | Me | " | | H | H | H | T2 | |
| 309 | Me | " | | H | H | Na | T2 | |
| 310 | Me | (cyclohexane-1,3-dione group) | | H | H | H | T1 | 153–155 (decomp.) |
| 311 | Me | " | | H | H | Na | T1 | >280 |
| 312 | Me | " | | H | H | H | T2 | |
| 313 | Me | " | | H | H | Na | T2 | |

TABLE 1-continued

Compounds of the formula (1)

(1)

[Structure: benzene ring with COOR¹ group, R²R³C=N-NR⁴- substituent, and -SO₂-N(M)-C(O)-N(R⁶)-Het group]

| Ex. No. | R¹ | R² | R³ | R⁴ | R⁶ | M | Het | m.p. |
|---|---|---|---|---|---|---|---|---|
| 314 | Me | [2,2-dimethyl-1,3-dioxane-4,6-dione-like structure with Me, Me, and two acetate groups] | | H | H | H | T1 | 196–198 (decomp.) |
| 315 | Me | " | | H | H | Na | T1 | 229–234 (decomp.) |
| 316 | Me | " | | H | H | H | T2 | |
| 317 | Me | " | | H | H | Na | T2 | |
| 318 | Me | [cyclohexanone] | | H | H | H | T1 | |
| 319 | Me | [cyclohexanone] | | H | H | Na | T1 | |
| 320 | Me | " | | H | H | H | T2 | |
| 321 | Me | " | | H | H | Na | T2 | |
| 322 | Me | [piperidin-2-one] | | H | H | H | T1 | |
| 323 | Me | " | | H | H | Na | T1 | |
| 324 | Me | " | | H | H | H | T2 | |
| 325 | Me | " | | H | H | Na | T2 | |
| 326 | Me | [Me-C(=N-N(Me)-C(=O)Me)] | | H | H | H | T1 | |
| 327 | Me | " | | H | H | Na | T1 | |
| 328 | Me | " | | H | H | H | T2 | |
| 329 | Me | " | | H | H | Na | T2 | |
| 330 | Me | [Me-C(=N-Me)-O-C(=O)-Me] | | H | H | H | T1 | |
| 331 | Me | " | | H | H | Na | T1 | |
| 332 | Me | " | | H | H | H | T2 | |
| 333 | Me | " | | H | H | Na | T2 | |

TABLE 1-continued

Compounds of the formula (1)

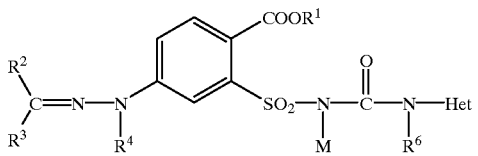

(1)

| Ex. No. | R¹ | R²  R³ | R⁴ | R⁶ | M | Het | m.p. |
|---|---|---|---|---|---|---|---|
| 334 | Me | 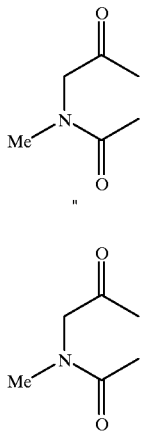 | H | H | H | T1 | |
| 335 | Me | " | H | H | Na | T1 | |
| 336 | Me | 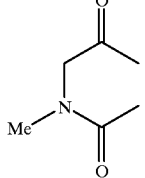 | H | H | H | T2 | |
| 337 | Me | " | H | H | Na | T2 | |
| 338 | Me | 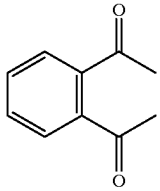 | H | H | H | T1 | 162–165 (decomp.) |
| 339 | Me | " | H | H | Na | T1 | 190–192 (decomp.) |
| 340 | Me | " | H | H | H | T2 | |
| 341 | Me | " | H | H | Na | T2 | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and part by weight of sodium oleoylmethyltaurate as wetting agent and dispersant, and grinding the mixture in a pinned-disk mill.

c) A dispersion concentrate which is readily dipsersible in water is obtained by mixing 20 parts by weight of a compound of the formula (I) with 6 parts by weight of alkylphenyl polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the miaure in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Granules which are dispersible in water are obtained by mixing
   75 parts by weight of a compound of the formula (I),
   10 parts by weight of calcium lignosulfonate,
   5 parts by weight of sodium lauryl sulfate,
   3 parts by weight of polyvinyl alcohol and
   7 parts by weight of kaolin, grinding the mixture on a pinned-disk mill and granulating the powder in a fluidized bed by spraying on water as granulation liquid.

f) Water-dispersible granules are also obtained by homogenizing, on a colloid mill,
   25 parts by weight of a compound of the formula (I)
   5 parts by weight of sodium 2,2'-dinaphthylmethane,-6,6'-disulfonate,
   2 parts by weight of sodium oleoylmethyltaurate, 1 part by weight of polyvinyl alcohol, 17 parts by weight of calcium carbonate and 50 parts by weight of water, precomminuting the mixture, subsequently grinding it on a bead mill and atomizing and drying the resulting suspension in a spray tower by means of a single-substance nozzle.

C) Biological Examples

1. Premergence Effect on Weeds

Seeds or rhizome pieces of monocotyledonous and dicotyledonous weed plants are placed in sandy loam soil in plastic pots covered with soil. The compounds according to the invention which have been fomulated in the form of wettable powders or emulsion concentrates are then applied to the surface of the soil cover in the form of aqueoss or emulsions at an application rate of 600 to 800 I of water/h (converted), in various dosages.

After the treatment, the pots are placed in a greenhouse and kept under good growth conditions for the weeds. After the test plants have emerged after a test period of 3 to 4 weeks, the damage to the plants or the negative effect on the emergence is scored visually by comparison with untreated controls. As shown by the test results, the compounds according to the invention have a good herbicidal pre-emergence activity against a broad spectrum of grass weeds and broad-leaved weeds. For example, the compounds of Preparation Examples Nos.: 5, 6, 17, 18, 42, 43, 46, 47, 58, 59,67, 74,75, 112, 113, 150, 151, 166, 186, 187, 198, 215, 302, 303, 310, 311, 314, 315, 338 and 339 (see Table 1) show a very good herbicidal activity against harmful plants such as Sinapis alba, Chrysanthemum segetum, Avena sativa, Stellaria media, Echinochloa crus-galli, Lolium multiflorum, Setaria spp., Abutilon theophrasti, Amaranthus retroflexus and Panicum miliaceum when applied pre-emergence at a rate of application of 0.3 kg and less of active ingredient per hectare.

2. Post-emergence Effect on Weeds

Seeds or rhizome pieces of monocotyledonous and dicotyedonous weeds are placed in sandy loam soil in plastic pots, covered with soil and grown in a greenhouse under good growth conditions. Three weeks after sowing, the test plants are treated in the three-leaf stage. The compounds according to the invention which have been formulated as wettable powders or as emulsion concentrates are sprayed in various dosages onto the green parts of the plants at an application rate of 600 to 800 1 of water/ha (converted). After the test plants have remained in the greenhouse for about 3 to 4 weeks under ideal growth conditions, the effect of the preparations is scored visually by comparison with untreated controls. The agents according to the invention also have a good herbicidal post-emergence activity against a broad spectrum of economically important grass weeds and broad-leaved weeds. For example the compounds of Preparation Examples Nos. 5, 6, 17, 18, 42, 43, 46, 47, 58, 59, 67, 74, 75, 112, 113, 150, 151, 166, 186, 187, 198, 215, 302, 303, 310, 311, 314, 315, 338 and 339 (see Table 1) show very good herbicidal activity against harmful plants such as *Sinapis alba, Echinochloa crus-galli, Lolium multiflorum, Chrysanthemum segetum*, Setaria spp., *Abutilon theophrast, Amaranthus retroflexus, Panicum miliaceum and Avena sativa* when applied post-emergence at an application rate of 0.3 kg and less of active ingredient per hectare.

3. Tolerance by Crop Plants

In further greenhouse experiments, seeds of a substantial number of crop plants and weeds are placed in sandy loam soil and covered with soil. Some of the pots are treated immediately as described in Section 1, and the remaining pots are placed in a greenhouse until the plants have developed two to three true leaves and are then sprayed with various dosages of the substances of the formula (I) according to the invention as described in Section 2. Visual scoring four to five weeks after application and after the plants have remained in the greenhouse reveals that the compounds according to the invention did not inflict any damage to dicotyledonous crops such as soya-beans, cotton, oilseed rape, sugar beet and potatoes when used pre- and post-emergence, even when high dosages of active substance were used. Moreover, some substances also leave Gramineae crops such as barley, wheat, rye, millets, maize or rice unharmed. Some of the compounds of the formula (I) have a high selectivity and are therefore suitable for controlling undesirable vegetation in agricultural crops.

What is claimed is:

1. A compound of the formula (I) or a salt thereof

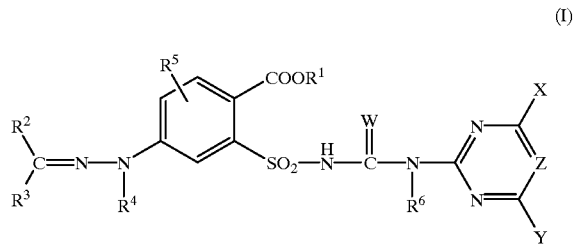

(I)

in which

R$^1$ is H or a hydrocarbon radical which is unsubstituted or substituted, or a heterocyclyl radical which is unsubstituted or substituted, where each of the last two-mentioned radicals including substituents has 1 to 20 carbon atoms, R$^2$ and R$^3$ for the definition of R$^2$ and R$^3$ one of the following combinations a, b, or c applies:

a) R$^2$ is CN, NO$_2$ or acyl and
R$^3$ is CN, NO$_2$, acyl, CF$_3$, a substituted or unsubstituted monocyclic, bicyclic or polycyclic aryl radical having from 6 to 20 carbon atoms including substituents, or a substituted or unsubstituted heterocycle, b) CR$^2$R$^3$ together form a ring having 3 to 8 ring atoms which is carbocyclic or heterocyclic and has one heteroatom selected from the group consisting of O, N, S, SO, or SO$_2$ or is a heterocycle selected from the group consisting of piperidyl, piperazinyl, dioxolanyl, morpholinyl; or from the following heterocyclic rings:

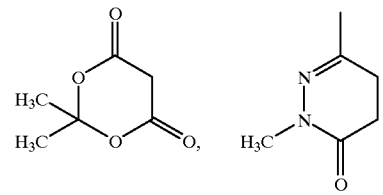

wherein
said rings have at least one carbon atom substituted by an oxo group in a position adjacent to the carbon atom in 1-position of the CR$^2$R$^3$ and is optionally further substituted by one or more radicals selected from the group consisting of (C$_1$–C$_4$)alkyl, (C$_1$–C$_4$)haloalkyl, halogen, and oxo;

c) $R^2$ is $NO_2$ or $[(C_1–C_4)$alkyl]carbonyl and
$R^3$ is H or $(C_1–C_4)$alkyl,
$R^4$ is H or an aliphatic hydrocarbon radical having 1 to 6 carbon atoms in the hydrocarbon moiety where the last-mentioned radical is unsubstituted or substituted by one or more radicals are selected from the group consisting of halogen, $(C_1–C_4)$alkoxy, $(C_1–C_4)$alkylthio, $(C_1–C_4)$alkylsulfonyl, $[(C_1–C_4)$alkyl]carbonyl, $[(C_1–C_4)$alkoxy]carbonyl, CN, substituted or unsubstituted phenyl, unsubstituted or substituted $(C_3–C_6)$cycloalkyl, $(C_3–C_6)$alkenyl or $(C_3–C_6)$alkynyl or an acyl radical,
$R^5$ is H, halogen, $NO_2$, CN, $(C_1–C_4)$alkyl, $(C_1–C_4)$alkoxy, $[(C_1–C_4)$alkyl]carbonyl or $[(C_1–C_4)$alkoxy]carbonyl, where each of the four last-mentioned radicals is unsubstituted or substituted in the alkyl moiety by one or more halogen atoms,
$R^6$ is H or $(C_1–C_4)$alkyl,
W is an oxygen or sulfur atom,
X, Y independently of one another are H, halogen, $(C_1–C_4)$alkyl, $(C_1–C_4)$alkoxy, $(C_1–C_4)$alkylthio, where each of the 3 last-mentioned radicals is unsubstituted or substituted by one or more radicals selected from the group consisting of halogen, $(C_1–C_4)$alkoxy and $(C_1–C_4)$alkylthio, or is mono- or di[$(C_1–C_4)$alkyl]amino, $(C_3–C_6)$cycloalkyl, $(C_2–C_5)$alkenyl, $(C_3–C_5)$alkynyl, $(C_3–C_5)$alkenyloxy or $(C_2–C_5)$alkynyloxy and
Z is CH,
and wherein
said substituents for the hydrocarbon or aryl radicals, unless otherwise defined, are halogen, alkyl, alkenyl, alkynyl, cycloalkyl, alkoxy, haloalkoxy, alkylthio, hydroxyl, amino, nitro, carboxyl, cyano, azido, alkoxycarbonyl, alkylcarbonyl, formyl, carbamoyl, mono- and dialkylamninocarbonyl, acylamino, mono- and dialkylamino, alkylsulfinyl, haloalkylsulfinyl, alkylsulfonyl, haloakylsulfonyl, haloalkyl, haloalkenyl, haloalkynyl, alkenyloxy, alkynyloxy, phenoxy, optionally substituted aryl, and optionally substituted heterocycle,
heterocycle, unless otherwise defined, is a saturated or unsaturated ring having from 3 to 7 ring atoms having one ring atom selected from the groups consisting of N, O, S, SO, and $SO_2$ or is a heteroaromatic radical having 5 or 6 ring atoms having one ring atom selected from the group consisting of N, O or S; or is a heterocycle selected from the group consisting of pyrimidinyl, pyradazinyl, pyrazinyl, thiazole, oxazole, pyrazolyl, imidazole, piperidyl, piperazinyl, dioxolanyl and morpholinyl; and
the substituents for the heterocyclic groups are the same as identified above for the hydrocarbon and the aryl radicals or oxo; and
acyl is a formyl or is a radical of an organic acid having 1 to 20 carbon atoms, said radical being optionally substituted by the hydrocarbyl or aryl substituents, identified above, and is selected from the group consisting of carboxylic acid, thiocarboxylic acid, N-substituted iminocarboxylic acid, carbonic monoesters, N-substituted carbamic acid, sulfonic acid, sulfinic acid, phosphonic acid, and phosphinic acid.

2. The compound or its salt as claimed in claim 1, wherein
$R_1$ is H, $(C_1–C_6)$alkyl, $(C_3–C_6)$alkenyl, $(C_3–C_6)$alkynyl, where each of the three last-mentioned radicals is unsubstituted or substituted by one or more radicals selected from the group consisting of halogen, phenyl, $(C_1–C_4)$alkoxy, $(C_1–C_4)$alkylthio and $[(C_1–C_4)$alkoxy]carbonyl, or is $(C_3–C_6)$cycloalkyl, $(C_3–C_6)$cycloalkyl $(C_1–C_3)$alkyl, heterocyclyl having 3 to 6 ring atoms or heterocyclyl$(C_1–C_3)$alkyl having 3 to 6 ring atoms, where each of the 4 last-mentioned radicals is unsubstituted or substituted by one or more radicals selected from the group consisting of halogen, $(C_1–C_4)$alkyl and $(C_1–C_4)$alkoxy,
$R^2$ and $R^3$ for the definition of $R^2$ and $R^3$ one of the following combinations a, b, or c applies:
a) $R^2$ is $[(C_1–C_4)$alkyl]carbonyl which is unsubstituted or substituted by one or more radicals selected from the group consisting of halogen, $(C_1–C_4)$alkoxy, $(C_1–C_4)$alkylthio and phenyl, or is $[(C_1–C_4)$alkoxy]carbonyl which is unsubstituted or substituted by one or more radicals selected from the group consisting of halogen, $(C_1–C_4)$alkoxy, phenoxy and phenyl, or is $CONR^7R^8$, CHO, CN, $NO_2$ or phenylcarbonyl which is unsubstituted or substituted by one or more radicals selected from the group consisting of halogen, $(C_1–C_4)$alkyl, $(C_1–C_4)$haloalkyl, $(C_1–C_4)$alkoxy, $(C_1–C_4)$alkylthio, CN and $NO_2$, or is $(C_1–C_4)$alkylsulfonyl, $(C_1–C_4)$haloalkylsulfonyl or —P(O)[O$(C_1–C_4)$alkyl]$_2$ and
$R^3$ is as defined under $R^2$ or is $CF_3$ or phenyl which is unsubstituted or substituted by one or more radicals selected from the group consisting of halogen, $(C_1–C_4)$alkyl, $(C_1–C_4)$haloalkyl, $(C_1–C_4)$alkoxy, $(C_1–C_4)$alkylthio, $(C_1–C_4)$alkylsulfonyl, $[(C_1–C_4)$alkoxy]carbonyl, CN and $NO_2$, or
b) $R^2R^3C$ together form a ring having 5 to 8 ring atoms, which is carbocyclic or heterocyclic and has one heteroatom selected from the group consisting of N, O and S and which is substituted by one or two oxo groups, in each case in the position alpha to the carbon atom in the 1-position of the group $CR^2R^3$ and is further optionally substituted by one or more radicals selected from the group consisting of $(C_1–C_4)$alkyl, $(C_1–C_4)$haloalkyl, halogen and oxo, or
c) $R^2$ is $NO_2$ or $[(C_1–C_4)$alkyl]carbonyl and
$R^3$ is H or $(C_1–C_4)$alkyl,
$R^4$ is H or $(C_1–C_6)$alkyl which is unsubstituted or substituted by one or more radicals selected from the group consisting of halogen, $(C_1–C_4)$alkoxy, $(C_1–C_4)$alkylthio, $(C_1–C_4)$alkylsulfonyl, $[(C_1–C_4)$alkoxy]carbonyl, CN, phenyl and $(C_3–C_6)$cycloalkyl, or is $(C_3–C_6)$alkenyl or $(C_3–C_6)$alkynyl, where each of the two last-mentioned radicals is unsubstituted or substituted by one or more halogen atoms, or is a group of the formula

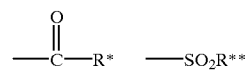

in which
$R^*$ is H, $(C_1–C_8)$alkyl, $(C_2–C_6)$alkenyl, $(C_2–C_6)$alkynyl, where each of the three last-mentioned radicals is unsubstituted or substituted by one or more radicals selected from the group consisting of halogen, $(C_1–C_4)$alkoxy, ($C_1$–$C_4$)alkylthio, phenoxy, [($C_1$–$C_4$)alkoxy] carbonyl, unsubstituted or substituted heterocyclic radical, unsubstituted or substituted phenyl, where the substituents are selected from the group consisting of halogen, CN, $NO_2$, ($C_1$–$C_4$)alkyl, ($C_1$–$C_4$)alkoxy, and ($C_1$–$C_4$)haloalkyl, or is unsubstituted or substituted ($C_3$–$C_6$)cycloalkyl, where the substituents are selected from the group consisting of halogen, CN, $NO_2$, ($C_1$–$C_4$)alkyl, ($C_1$–$C_4$)alkoxy, and ($C_1$–$C_4$)haloalkyl, $R^{**}$ is ($C_1$–$C_6$)alkyl, ($C_3$–$C_6$)alkenyl, ($C_3$–$C_6$)alkynyl, where each of the three last-mentioned radicals is unsubstituted or substituted by one or more radicals selected from the group consisting of halogen, ($C_1$–$C_4$)alkoxy, ($C_1$–$C_4$)alkylthio and phenyl, or is phenyl which is unsubstituted or substituted by one or more radicals selected from the group consisting of halogen, CN, $NO_2$, ($C_1$–$C_4$)alkyl, ($C_1$–$C_4$)haloalkyl and ($C_1$–$C_4$)alkoxy, $R^7$ and $R^8$ independently of one another are H, ($C_1$–$C_4$)alkyl, ($C_3$–$C_4$)alkenyl, ($C_3$–$C_4$)alkynyl or phenyl which is unsubstituted or substituted by one or more radicals selected from the group consisting of halogen, ($C_1$–$C_4$) alkyl, ($C_1$–$C_4$)haloalkyl, ($C_1$–$C_4$)alkoxy, ($C_1$–$C_4$)alkylthio, ($C_1$–$C_4$)alkylsulfonyl, [($C_1$–$C_4$)alkoxy]carbonyl, CN and $NO_2$, or $R^7$ and $R^8$ together with the nitrogen atom form a heterocyclic ring having 5 or 6 ring members, which is unsubstituted or mono- or polysubstituted by ($C_1$–$C_4$)alkyl or an oxo group, W is O or S, and X and Y independently of one another are H, halogen, ($C_1$–$C_4$)alkyl, ($C_1$–$C_4$)alkoxy ($C_1$–$C_4$)alkylthio, where each of the three last-mentioned radicals is unsubstituted or substituted by one or more radicals selected from the group consisting of halogen, ($C_1$–$C_3$)alkoxy and ($C_1$–$C_4$)alkylthio, mono- or di[($C_1$–$C_4$) alkyl]amino, ($C_3$–$C_6$)cycloalkyl, ($C_3$–$C_5$) alkenyl, ($C_3$–$C_5$)alkenyloxy or ($C_3$–$C_5$) alkynyloxy.

3. A compound or a salt thereof as claimed in claim 1, wherein $R^1$ is ($C_1$–$C_6$)alkyl which is unsubstituted or substituted by one or more radicals selected from the group consisting of halogen and ($C_1$–$C_4$)alkoxy, or is 3-oxetanyl, ($C_3$–$C_4$)alkenyl or ($C_3$–$C_4$)alkynyl, a) $R^2$ and $R^3$ independently of one another are [($C_1$–$C_4$) alkyl]carbonyl, [($C_1$–$C_4$)alkoxy]carbonyl, $CONR^7R^8$ CHO, CN, $NO_2$, benzoyl or ($C_1$–$C_4$) alkylsulfonyl or b) $CR^2R^3$ together form a ring having 5 to 8 ring atoms, which is carbocyclic or heterocyclic and has one heteroatom selected from the group consisting of N, O and S and which is substituted by one or two oxo groups, in each case in the position alpha to the carbon atom in the 1-position of the group $CR^2R^3$ and said ring is optionally further substituted by one or more radicals selected from the group consisting of ($C_1$–$C_4$alkyl, ($C_1$–$C_4$)haloalkyl and halogen, or c) $R^2$ is $NO_2$ or [($C_1$–$C_4$)alkyl]carbonyl and $R^3$ is H or ($C_1$–$C_4$)alkyl, $R^4$ is H, ($C_1$–$C_4$)alkyl which is unsubstituted or substituted by one or more radicals selected from the group consisting of halogen, ($C_1$–$C_4$)alkoxy, ($C_1$–$C_4$)alkylthio, [($C_1$–$C_4$)alkoxy]carbonyl and phenyl or is ($C_3$–$C_4$)alkenyl or ($C_3$–$C_4$)alkynyl, $R^5$ is H, ($C_1$–$C_4$)alkyl, ($C_1$–$C_4$)haloalkyl, ($C_1$–$C_4$) alkoxy or halogen, X and Y independently of one another are ($C_1$–$C_4$) alkyl, ($C_1$–$C_4$)alkoxy, where each of the two last-mentioned radicals is unsubstituted or substituted by one or more halogen atoms, or are ($C_1$–$C_4$) alkylthio, halogen or mono- or di[($C_1$–$C_2$)alkyl] amino and W is an oxygen atom.

4. The compound or a salt thereof as claimed in claim 1, wherein $R^1$ is methyl or ethyl, $R^2$ and $R^3$ independently of one another are [($C_1$–$C_2$) alkoxy]carbonyl, CN or $NO_2$ or $CR^2R^3$ together form a ring having 5 or 6 ring atoms, which is carbocyclic or heterocyclic and has one heteroatom selected from the group consisting of N, O and S and which is substituted by one or two oxo groups, in each case in the position alpha to the carbon atom in 1-position of the group $CR^2R^3$, and said ring is optionally substituted by one or more ($C_1$–$C_2$)alkyl radicals, and $R^4$ is H, $R^5$ is H, ($C_1$–$C_4$)alkyl or halogen, X is ($C_1$–$C_2$)alkyl, ($C_1$–$C_2$)alkoxy, ($C_1$–$C_2$)alkylthio, ($C_1$–$C_2$)haloalkyl or ($C_1$–$C_2$)haloalkoxy and Y is ($C_1$–$C_2$)alkyl, ($C_1$–$C_2$)alkoxy, halogen, $NHCH_3$ or $N(CH_3)_2$.

5. A herbicidal or plant-growth-regulating composition, which comprises one or more compounds of the formula (I) or a salt thereof as claimed in claim 1 and formulation auxiliaries customary in crop protection.

6. A method for controlling harmful plants or for regulating the growth of plants, which comprises applying an effective amount of one or more compounds of the formula (I) or a salt thereof as claimed in claim 1 to the harmful plants, to seeds thereof or to the area where they grow.

* * * * *